(12) United States Patent
Yang et al.

(10) Patent No.: US 11,006,557 B2
(45) Date of Patent: May 11, 2021

(54) CLOTH ELECTRONIZATION PRODUCT AND METHOD

(76) Inventors: Chang-Ming Yang, Taiwan (TW); Chunmei Chou, Miaoli (TW)

(*) Notice: Subject to any disclaimer, the term of this patent is extended or adjusted under 35 U.S.C. 154(b) by 155 days.

(21) Appl. No.: 14/114,700

(22) PCT Filed: Apr. 28, 2012

(86) PCT No.: PCT/CN2012/000574
§ 371 (c)(1),
(2), (4) Date: Oct. 29, 2013

(87) PCT Pub. No.: WO2012/146066
PCT Pub. Date: Nov. 1, 2012

(65) Prior Publication Data
US 2014/0084045 A1    Mar. 27, 2014

(30) Foreign Application Priority Data

Apr. 29, 2011  (WO) ................ PCT/CN2011/000758

(51) Int. Cl.
B29C 65/00  (2006.01)
B29C 65/02  (2006.01)
(Continued)

(52) U.S. Cl.
CPC .......... H05K 13/00 (2013.01); A61B 5/6804 (2013.01); A61N 1/0484 (2013.01); A61N 1/16 (2013.01);
(Continued)

(58) Field of Classification Search
CPC ..... A61B 5/6804; A61B 5/6805; A61B 5/389; A61B 5/02055; A61B 5/02438;
(Continued)

(56) References Cited

U.S. PATENT DOCUMENTS 4,158,103 A  6/1979  Danilin et al.
4,315,111 A  2/1982  Thomas
(Continued)

FOREIGN PATENT DOCUMENTS

CN  1407571 A  4/2003
CN  1650057 A  8/2005
(Continued)

OTHER PUBLICATIONS

International Search Report for corresponding International Application No. PCT/CN2012/000574, dated Aug. 9, 2012 (8 pages).
(Continued)

*Primary Examiner* — Philip C Tucker
*Assistant Examiner* — Brian R Slawski
(74) *Attorney, Agent, or Firm* — Chun-Ming Shih; HDLS IPR Services

(57) ABSTRACT

Cloth electronic product, by which physiological information can be examined through cloth, includes a packaging cloth or a heat melt adhesive film as circuit, at least an electronic component, such as resistors, microprocessors and sensing assembly, etc., at least a transmission line to be connected with the conductive region of electronic component. Method of producing a cloth electronic product includes sewing the electronic component on packaging cloth or heat melt adhesive film after being connected with the transmission line, or connecting electronic component with the transmission line during the process of jointing of transmission or sewing of packaging cloth or heat melt adhesive film, and then sewing the packaging cloth on the clothing cloth or integrating the heat melt adhesive film into the packaging cloth or clothing cloth. Original structure of the heat melt adhesive film cannot be viewed and miniaturization effects can be produced.

30 Claims, 18 Drawing Sheets

(51) Int. Cl.

| | |
|---|---|
| *B32B 37/00* | (2006.01) |
| *B32B 38/00* | (2006.01) |
| *B32B 7/08* | (2019.01) |
| *B32B 38/14* | (2006.01) |
| *C08J 5/00* | (2006.01) |
| *H05K 13/00* | (2006.01) |
| *A61B 5/00* | (2006.01) |
| *A61N 1/04* | (2006.01) |
| *A61N 1/16* | (2006.01) |
| *D05B 23/00* | (2006.01) |
| *B29C 65/62* | (2006.01) |
| *B32B 27/12* | (2006.01) |
| *B29C 65/40* | (2006.01) |
| *B29C 65/48* | (2006.01) |
| *B29C 65/72* | (2006.01) |
| *A61B 5/0205* | (2006.01) |
| *A61B 5/024* | (2006.01) |
| *A61B 5/08* | (2006.01) |
| *A61B 5/389* | (2021.01) |

(52) U.S. Cl.
CPC .......... *D05B 23/00* (2013.01); *A61B 5/02055* (2013.01); *A61B 5/02438* (2013.01); *A61B 5/0816* (2013.01); *A61B 5/389* (2021.01); *A61B 2560/0443* (2013.01); *A61B 2562/0219* (2013.01); *A61B 2562/12* (2013.01); *A61B 2562/18* (2013.01); *B29C 65/40* (2013.01); *B29C 65/4815* (2013.01); *B29C 65/62* (2013.01); *B29C 65/72* (2013.01); *B32B 27/12* (2013.01); *B32B 2307/202* (2013.01); *Y10T 156/10* (2015.01)

(58) Field of Classification Search
CPC .......... A61B 5/0816; A61B 2560/0443; A61B 2562/0219; A61B 2562/12; A61B 2562/18; H05K 1/038; H05K 13/00; H05K 13/0023; B29C 65/00; B29C 65/02; B29C 65/40; B29C 65/48; B29C 65/4815; B29C 65/50; B29C 65/62; B29C 65/72; D05B 23/00; A61N 1/0484; A61N 1/16; Y10T 156/10; B32B 2307/202; B32B 27/12
USPC .. 156/60, 64, 70, 91, 92, 93, 277, 297, 298, 156/299, 300, 308.2, 309.6; 228/175; 112/475.08, 475.09; 600/388, 389
See application file for complete search history.

(56) References Cited

U.S. PATENT DOCUMENTS

| | | | | |
|---|---|---|---|---|
| 4,937,883 A | * | 7/1990 | Shirai | A41D 13/0015 2/113 |
| 5,105,478 A | * | 4/1992 | Pyc | A41D 27/28 2/106 |
| 5,144,534 A | * | 9/1992 | Kober | H05K 3/4691 174/254 |
| 5,881,547 A | | 3/1999 | Chiou et al. | |
| 6,210,771 B1 | * | 4/2001 | Post | H05K 3/10 139/1 R |
| 6,493,933 B1 | | 12/2002 | Post et al. | |
| 6,687,523 B1 | * | 2/2004 | Jayaramen | A41D 13/1281 600/388 |
| 6,727,197 B1 | * | 4/2004 | Wilson | G06K 19/041 174/117 F |
| 6,729,025 B2 | * | 5/2004 | Farrell | B32B 5/02 29/825 |
| 6,856,715 B1 | | 2/2005 | Ebbesen et al. | |
| 6,957,525 B2 | | 10/2005 | Verstraeten et al. | |
| 7,025,596 B2 | | 4/2006 | Zollo et al. | |
| 7,248,756 B2 | | 7/2007 | Ebbesen et al. | |
| 7,592,270 B2 | | 9/2009 | Hill et al. | |
| 8,298,968 B2 | | 10/2012 | Swallow et al. | |
| 2003/0211797 A1 | * | 11/2003 | Hill | H05K 1/189 442/205 |
| 2003/0212319 A1 | | 11/2003 | Magill | |
| 2004/0259391 A1 | | 12/2004 | Jung et al. | |
| 2005/0029680 A1 | * | 2/2005 | Jung | H05K 3/284 257/787 |
| 2006/0254811 A1 | * | 11/2006 | Kirstein | H05K 1/038 174/256 |
| 2006/0290497 A1 | | 12/2006 | Sugata | |
| 2007/0020445 A1 | * | 1/2007 | Liu | B81C 99/008 428/195.1 |
| 2007/0119539 A1 | * | 5/2007 | Gunzel | B29C 65/4815 156/300 |
| 2008/0131669 A1 | * | 6/2008 | Michalk | B32B 27/12 428/196 |
| 2009/0018428 A1 | * | 1/2009 | Dias | A41D 13/1281 600/388 |
| 2009/0176425 A1 | * | 7/2009 | Chou | B32B 3/02 442/110 |
| 2009/0306485 A1 | * | 12/2009 | Bell | A61B 5/04085 600/301 |
| 2010/0147562 A1 | * | 6/2010 | Chu | B32B 38/0004 174/254 |
| 2010/0149767 A1 | * | 6/2010 | Biesheuvel | H01R 4/58 361/760 |
| 2010/0259925 A1 | | 10/2010 | Hsu et al. | |
| 2010/0302745 A1 | * | 12/2010 | Hsu | H05K 3/32 361/749 |
| 2011/0282164 A1 | | 11/2011 | Yang et al. | |
| 2012/0215076 A1 | | 8/2012 | Yang et al. | |
| 2012/0247868 A1 | | 10/2012 | Kato et al. | |

FOREIGN PATENT DOCUMENTS

| | | | | |
|---|---|---|---|---|
| CN | 1252762 C | | 4/2006 | |
| CN | 1882280 B | | 12/2006 | |
| CN | 201468043 U | | 5/2010 | |
| JP | 2003-512734 A | | 4/2003 | |
| KR | 1020100098156 | * | 9/2010 | B32B 7/02 |
| WO | 01/30123 A1 | | 4/2001 | |
| WO | 03/002682 A1 | | 1/2003 | |
| WO | 2005018365 A1 | | 3/2005 | |
| WO | 2006/060934 A1 | | 6/2006 | |
| WO | 2010/083630 A1 | | 7/2010 | |
| WO | 2011/020299 A1 | | 2/2011 | |

OTHER PUBLICATIONS

Official Action dated Dec. 14, 2015, issued by the Japan Patent Office in related Japanese Patent Application No. JP 2014-506726, with Google English machine translation (6 pages).
EPO Extended European Search Report dated Feb. 23, 2015, by the European Patent Office in corresponding European Patent Application No. EP-12776080.9 (9 pages).
Post, E. R., et al., "E-broidery: Design and fabrication of textile-based computing", IBM Systems Journal, vol. 39, Nos. 3 and 4; Dec. 31, 2000 (Dec. 31, 2000); XP002335110; ISSN: 0018-8670; pp. 840-860.
Office Action issued in corresponding JP Application No. 2014-506726 dated Jul. 31, 2018 (6 pages).

* cited by examiner

Figrue 5d

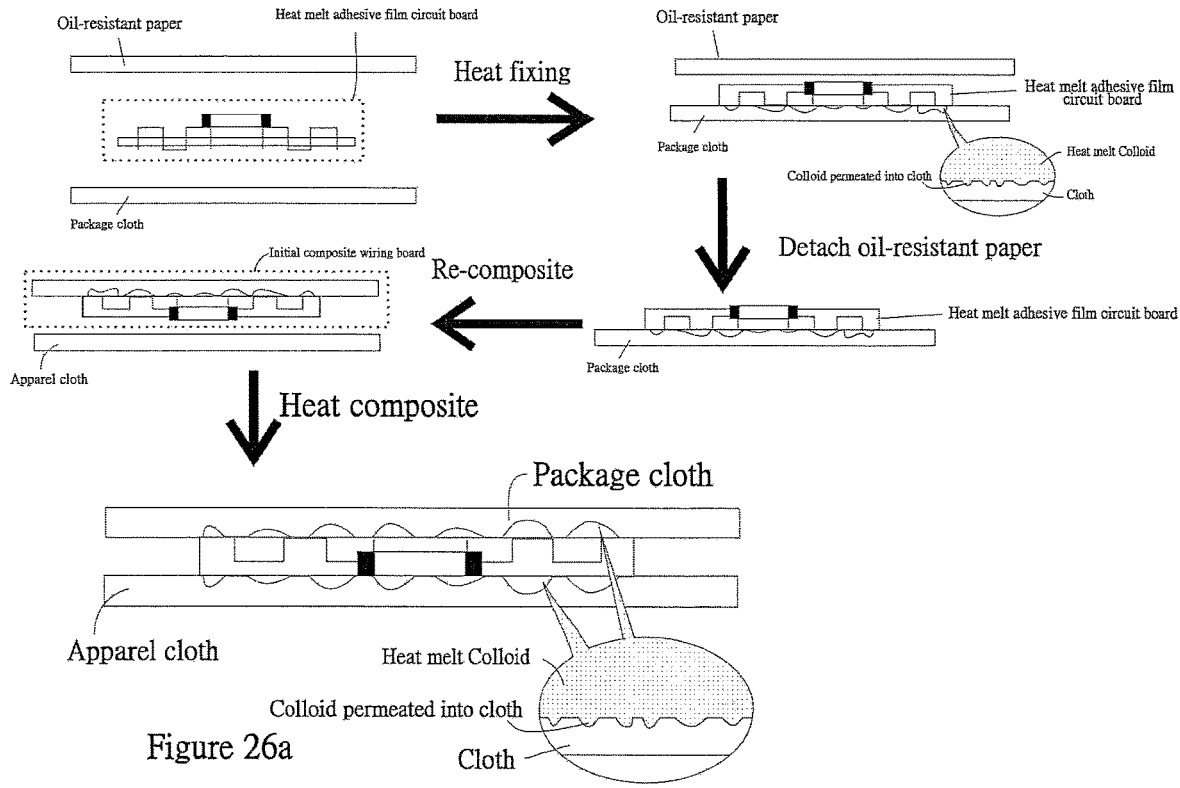
Figure 26a
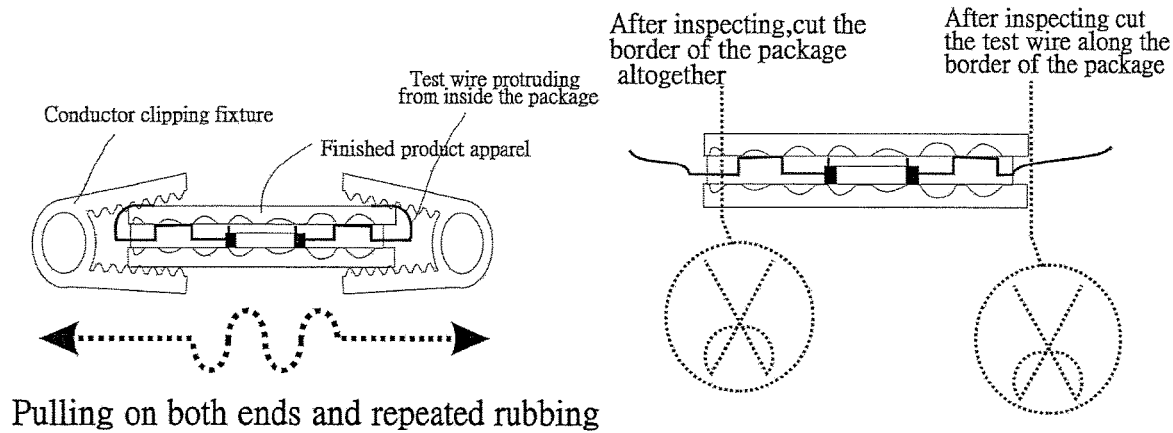
Figure 26b
Figure 26c

Regional multi-layer board
Equipping a regional ground wire on the upper layer of the sensitive signal wire, providing a shield layer

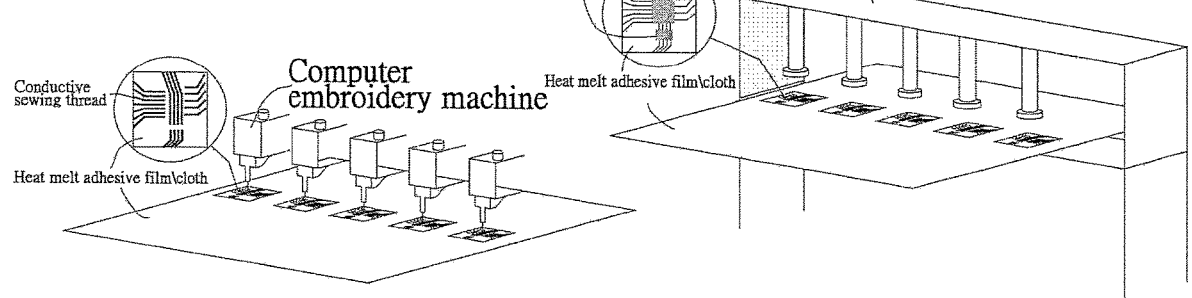
Figure 36a
Figure 36b
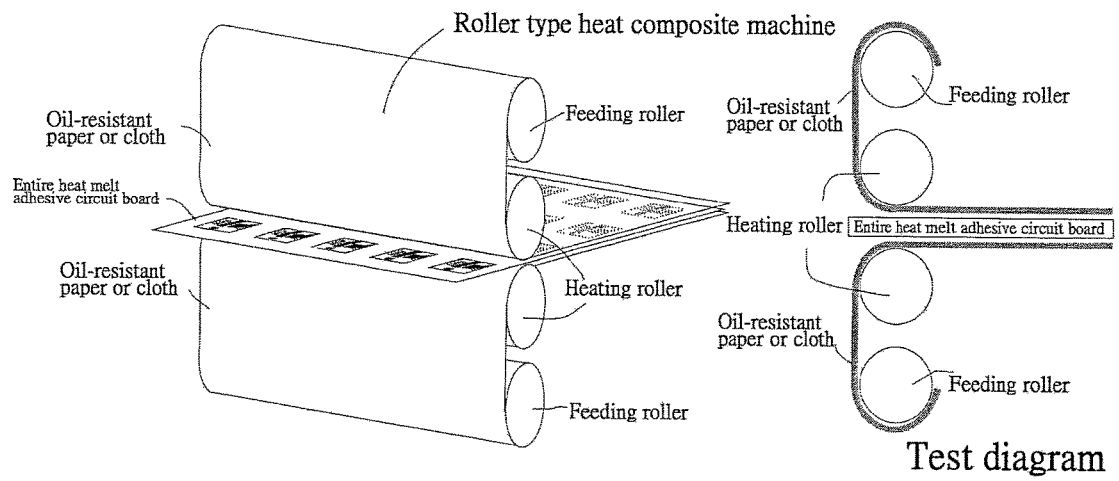
Figure 36c
Figure 36d

CLOTH ELECTRONIZATION PRODUCT AND METHOD

CROSS REFERENCE TO RELATED APPLICATIONS

This is a national stage application based on PCT/CN2012/000574, filed on Apr. 28, 2012, which claims priority to PCT/CN2011/000758, filed on Apr. 29, 2011. This application claims the priority of these prior applications and incorporates their disclosures by reference in their entireties.

AREAS OF TECHNOLOGY

This invention involves the products and methods of a type of cloth electronization. Specifically, it involves those in which the clothing for dresses and electronic modules and transmission lines are produced separately first, and then are stitched together seamlessly. More precisely, the circuit board consists of a cloth packaging material or heat melt adhesive film; electronic modules or transmission lines are first stitched onto or glued to the board, and the board is then sewn, glued, or heated up and fixed to the cloth used for dresses, so as to enable the cloth for electronic publishing, encapsulation and insulation, as well as for the protection of electronic modules.

BACKGROUND TECHNOLOGY

There are many conventional technologies that form electronic circuits by using wires to fix electronic modules to textile materials such as cloth or leather—for example, the American patent disclosure for U.S. Ser. No. 10/868,501 (construction and connection technique in textile structure). In that case, a metal board is used as a "bridge" to connect the electronic modules and the transmission wires. However, this method is complicated and requires a tin coating or welding, such that it does not meet the requirements of environmental protection. More than that, there is no insulator at the joints between the electronic modules and the cloth/transmission lines. Another U.S. Pat. No. 6,493,933 discloses a package in which a conductive wire is connected to every electronic module; meanwhile, the conductive wires are fixed to the cloth underneath by using a conductive transmission wire, and are connected with the transmission wires of other electronic modules. In this way, all the conductive transmission wires connected to the electronic module are insulated among themselves, thus fawning a circuit on the cloth. However, when the cloth or the electronic modules are under external forces, the conductive transmission threads and the conductive wires connected to the electronic modules are likely to fall apart and split open.

A different U.S. Pat. No. 7,025,596 discloses how an electronic module can be placed on a carrier first, with a transmission wire penetrating through the carrier. The conductive regions on the carrier and the transmission wires on the cloth are connected by another transmission wire, thus forming a circuit on the cloth. This method is also very complicated and its implementation requires a carrier. Therefore, it is likely to be influenced by external forces.

The U.S. Ser. No. 12/787,376 also requires the use of a base, with two pins extending out. The transmission wires are connected to the pins to form a circuit on the cloth. The U.S. Pat. No. 6,729,025 also places a circuit on the board, and then places the board on the cloth to form a circuit on the cloth.

U.S. patent Ser. No. 12/477,148 states that the connection between the circuit and the censor can be serpentine-like or concertina-like. But the actual structure of the circuit itself is not explained.

The U.S. Pat. No. 7,592,276 places electronic modules on the longitude threads as well as the latitude threads on the cloth, and the connection between electronic modules and signal wires is completed via the intersection of the longitude threads and latitude threads. As a result, the positions of the insulated threads in the electronic modules and those of the wires are restrained, and the electronic modules and signal wires, even when split open or fused, cannot be replaced. Besides, the conducting yarn 120 that shuttles up and down on the cloth, being connected to the functional yarn 150 to form an electronic module, is also not designed for insulation, and therefore, is vulnerable to outside interference.

According to the method described in the American patent numbered US2003/0212319A1, the transmission wires are sewn to the cloth, and the conductive regions on the electronic modules are connected to the transmission wires. However, the transmission wires 6 and 7 (as illustrated in FIG. 2) will come in contact with human skin. This will lead to blurred signals due to interference from the skin as well as from external friction. The American patent numbered US2010/0259925A1 disclosed a kind of illuminated textile product, which includes an illuminating device based on a diode and a textile construct. The illuminating device based on a diode has M contact points, and the textile construct offers conductive floating points corresponding to those M contact points. The transmission wires will contact human skin. The transmission has to be realized within a web-like circuit, and with a predetermined pattern. However, the circuit in this invention is non-web-like and can be designed freely.

The U.S. Pat. No. 4,158,103A and the Chinese patent numbered CN1650057A (US 2003/0211797A1) do not have packaging insulators in the conductive regions of the electronic modules, nor in the areas connected with transmission wires.

The U.S. Pat. No. 6,856,715 and the U.S. Pat. No. 7,248,756 disclose a pre-designed circuit, in which the connection between the electronic module and the transmission wires was not clearly explained. However, the transmission has to be realized within a web-like circuit, and with a predetermined pattern. At the same time, the circuit in this invention is non-web-like and can be designed freely.

The cloth currently available can be cotton, polyester, nylon, or plastic, among other materials. It can be further classified as conductive cloth, semi-conductive cloth, or non-conductive cloth. The formation of the cloth can be classified as being woven, knitted, tatted, embroidered, jacquard woven, or braided, among other formations. The commonly used materials for the transmission wires include metal fibers such as copper, gold, silver, nickel, aluminum, iron, stainless steel, and nickel alloy, among others. Other materials used include non-conductive fibers embedded or coated with conductive materials such as conductive carbon, nickel, copper, gold, silver, titanium, conductive multiple molecular materials, conductive wires, and so on. For example, the U.S. Pat. No. 5,881,547 discloses a conductive yarn that is made up of two stainless steel wires coated with a non-conductive electronic yarn.

The U.S. Pat. No. 6,957,525 discloses a conductive yarn that is made up of a wire of relatively high resistance on the inside, such as the stainless steel wire, plus a metal or alloy wire of relatively low resistance on the outside. According to what is disclosed in the U.S. patent Ser. No. 10/598,373, two wires are conductive only at the crossing points. However, their connection with the electronic modules is left unexplained.

According to the Chinese patent numbered CN1252762C, a metal wire and a fastener assembly are clipped together and fixed on the cloth as a switch. However, there is no mention of the fastener assembly used as a connector to connect the transmission wires and the electronic modules, let alone any mention of EMI produced by the fastener assembly.

As the Chinese patent numbered CN201468043U discloses, only an electronic chip is fixed to the clothing for dresses, directly using heat melt adhesive film. There is absolutely no mention of using the heat melt adhesive film as a circuit board for the layout of multiple electronic circuits.

According to the U.S. Pat. No. 4,315,111A, a leaf is fixed to a dress using Velcro, but no explanation is given for the packaging of the transmission wires or the dresses to which the wires are fixed.

The patent numbered US20120247868A1 just discloses a textile that absorbs various noises, among which electromagnetic waves are not likely to be reflected.

The patent numbered EP1399519A1 merely discloses synthetic adhesives, in particular, those conductive adhesives with conductive particles.

From the descriptions above, it should be clear that defects and a lack of convenience still exist in the methods, product structures, and applications of products and methods of cloth electronization, and that further improvements are urgently needed. To solve the problems noted above, related manufacturers have expended great efforts to figure out solutions. However, suitable designs have nonetheless yet to be developed after all this time, while commonly seen products and methods do not offer suitable solutions and structures to the questions mentioned previously, which obviously are what the professionals concerned can't wait to solve. Therefore, the question of how to create a new product and method for cloth electronization is indeed one of the most important research projects for the present time, and is also the objective that the industry currently needs urgent improvement on.

In this invention we did not use the welding of tin to realize the transit between the transmission wires and the electronic modules. In addition, various kinds of wires can be used as transmission wires. "Stitching" the transmission wires or electronic modules to the cloth also does not require any special method, which is to say that commonly-seen techniques, like plain weaving, knitting, tatting, embroidery, and so on, will do. The enamel-covered wires conventionally used now are formed by plastering conductors with heat melt adhesive films of electrically insulating varnishes and drying them by heat and it is very difficult to use the enamel-covered wires as the transmission wires on the cloth. In this invention we roll a yarn or multiple yarns around the enamel-covered wires to form protective layers, which therefore can be "stitched" to the cloth, so that the transmission wires are not likely to break even when the cloth is under external force (such as when the cloth is in a washer).

The methods of the cloth electronization mainly treat the cloth or the heat melt adhesive film as a "circuit board" to which various kinds of electronic modules (including resistance, capacitance, inductance, switch, 2 diode, amplifiers, analog/digital, digital/analog converter, processor, battery, sensors for temperature/breathing/heartbeat, electromyogram, acceleration gauge, gyroscope, microphone, camera, and so on, or other components, such as the medical instrument transcutaneous Nerve Stimulation (TENS), etc.) are fixed. Moreover, using the transmission wires, all these electronic modules are connected by joints without solder by means of knitting, plain weaving, tatting, gluing and so on, so as to fix the electronic modules to the cloth or the heat melt adhesive film, and to connect them with the transmission wires. In addition another layer of cloth on the cloth or the heat melt adhesive film is used to isolate the electronic circuits from contact with the outside world, thus preventing damage caused by external factors, or conditions like short circuit and interruption of circuit, from occurring. Based on the discussion above, there is a necessity for the cloth electronization. If the means of cloth electronization can be improved to make them simpler and more practical, the increased needs of the public will surely be met.

INVENTION CONTENTS

People need to put their clothes on most of the time in their daily lives. They come into contact with fabrics such as clothing, quilts, carpets, seats, steering wheels, seat belts, backpacks, masks, scarves, gloves, socks, hats, belts, caps, and so on, when they sit on chairs or lie on a bed. People's physiological information can also be checked via the cloth. As a result, intelligent textiles and attire are developing even more quickly.

Various electronic modules (such as resistance, capacitance, inductance, switch, 2 diode, amplifiers, analog/digital, digital/analog converter, processor, battery, sensors for temperature/breathing/heartbeat, electromyogram, acceleration gauge, gyroscope, microphone, camera and so on, or other components, such as temperature sensors, chemical sensors, biological sensors, pressure sensors, pressure, sound, electric fields, magnetic fields, and lightweight, acceleration and/or environmental conditions, intense source, power, heat, electromagnetic radiation and/or sound, infrared ways and/or wireless transmitter and/or receiver, imager, CCD imaging, thermocouple sensor, cooler, heater and/or generators, LCD components, electro-luminescent element, Organic Light Emitting element, OLED, Electrophoretic elements, LED, the piezo-electric element and/or sensors, microphone speakers, acoustic sensor, resistor, processors, digital signal processors, microprocessors, microcontrollers, CPU, analog-to-digital converters, Digital-to-Analog Converters, the data production equipment, the data application equipment, the process equipment, the switchboard, man-machine interface device, the input device for an individual, signal lights and/or flashing lights, battery, solar cells, photovoltaic power generation equipment, power, and addressing devices (such as the medical instrument transcutaneous Nerve Stimulation (TENS), etc.) are fixed to the cloth or the heat melt adhesive film. Moreover, using the transmission wires, all these electronic modules are connected by joints without solder by way of knitting, plain weaving, tatting, gluing and so on, so as to fix the electronic modules to the cloth or the heat melt adhesive film, and to connect them with the transmission wires. In addition, there is another layer of cloth on the cloth or the heat melt adhesive film to isolate electronic circuits from contact with the outside world, thus preventing damage caused by external factors, or conditions such as short circuits and interruption of circuit, from occurring.

This invention is intended to overcome the defects present in the products and methods of currently available cloth electronization, and to provide a new product and method for cloth electronization. The technical problems that need to be resolved are how to combine conventional cloth, conventional electronic modules, and currently available wire traversing technologies together, and how to use the cloth or the heat melt adhesive film as circuit boards, how to place electronic modules and the transmission wires on the cloth or the heat melt adhesive film, and then how to place the cloth or the heat melt adhesive film in the textiles or clothes, to electronize the cloth, which is highly feasible.

The invention is also intended to overcome the defects present in the products and methods of currently available cloth electronization, and to provide a new product and method for cloth electronization. The technical problems that need to be resolved include how to simplify the procedures of electronizing the cloth: the cloth or the heat melt adhesive film and the electronic modules or the transmission wires are produced separately first and then are combined together. Moreover, electronic modules and the transmission wires are combined together first, then are stitched to the cloth or the heat melt adhesive film, or are used to connect the electronic modules and the transmission wires together in the process of stitching or gluing the transmission wires to the cloth or the heat melt adhesive film. What comes next is to stitch another layer of cloth or the heat melt adhesive film on the cloth electronization to complete the sealing and make it insulated. That is to say, an electronic circuit is first placed on the packaging cloth or the heat melt adhesive film, then the packaging cloth or the heat melt adhesive film is stitched to a dress, or an electronic circuit is first placed on a dress or the heat melt adhesive film and is then covered by the packaging cloth or the heat melt adhesive to film to complete the packaging, insulation, waterproofing, formatting, and protection from the damages caused by the outside world. Moreover, none of the aforementioned methods involve material being "welded" onto the cloth. Therefore, none of them do any harm to the environment or the human body, nor do they cause any damage to the cloth, thus making this process more feasible.

This invention is intended to overcome the defects present in the products and methods of currently available cloth electronization, and to provide a new product and method for cloth electronization. The technical problems that need to be solved are how to use the heat melt adhesive film as circuit boards, how to fix electronic modules and the transmission wires to the heat melt adhesive film, and then how to merge the heat melt adhesive film into the cloth for attire or the packaging of the cloth, so as to complete the packaging, insulation, waterproofing, formatting, and protection from the damages caused by the outside world, and thus this process is more feasible.

This invention is intended to overcome the defects present in the products and methods of currently available cloth electronization, and to provide a new product and method for cloth electronization. The technical problems that need to be solved include how to easily change a damaged part when something is wrong with the electronic module, such that if s not necessary to throw away the entire piece of clothing, and thus this process is more feasible.

This invention is intended to overcome the defects present in the products and methods of currently available cloth electronization, and to provide a new product and method for cloth electronization. The technical problems that need to be solved include how to make the processor know immediately when the transmission wires break or have had a short circuit, and then how to fix such problems right away. For example, the electricity could be turned off immediately to prevent any harm to people, while the transmission wires can be exchanged with or replaced by backup transmission wires, so as to make it safer for the human body and easier to operate, and thus this process is more feasible.

This invention is intended to overcome the defects present in the products and methods of currently available cloth electronization, and to provide a new product and method for cloth electronization. The technical problems that need to be solved include how to realize the electronization of the cloth and the production of intelligent textiles, regardless of the type of cloth or method (i.e., plain weaving, knitting, tatting, embroidery, etc.) that is used, and how to keep the circuit intact and functioning normally in various external environments, such as in a washer, and thus this process is more feasible.

The objectives and the technical problems of this invention are realized by using the following technical plans. According to the invention, a product of the cloth electronization consists of a piece of cloth, at least one electronic module, and at least one transmission wire. That electronic module has a conductive region. The conductive region is first connected to the transmission wires, and then stitched to the packaging materials, and then stitched to or glued to the cloth for attire, or the conductive region is connected to transmission wires first, and then stitched to the cloth for attire, and then stitched to or glued to the packaging materials.

In addition, the objectives and the technical problems of this invention are realized by using the following technical plans. According to this invention, a product of the cloth electronization includes: a piece of cloth, at least one electronic module, and at least one transmission wire. Use the transmission wires and the technique that fixes electronic modules to the heat melt adhesive film to fix the transmission wires and electronic modules to the heat melt adhesive film. That electronic module has a conductive region, inside which the electronic modules are fixed to the heat melt adhesive film and are connected to the conductive regions in the transmission wires. The conductive regions in the electronic modules are connected to the transmission wires, and then the heat melt adhesive film is merged into the packaging materials or the cloth for the clothes.

The objectives and the technical problems of this invention are further realized by using the following technical plans.

In the aforementioned cloth electronization product, no welding is used in connecting the conductive regions in an electronic module on the cloth and the transmission wires, or in connecting the conductive regions in one electronic module and those in another electronic module, or in connecting the transmission wires.

In the aforementioned cloth electronization product, ways of connecting the conductive regions in electronic modules and the transmission wires include inter-wreathing, knotting, or point welding, and then the product of the cloth electronization is stitched to the cloth or placed on the heat melt adhesive film.

In the aforementioned cloth electronization product, various types of wires are used to stitch the electronic modules to the cloth or the heat melt adhesive film.

In the aforementioned cloth electronization product, glue or adhesives are used to fix the electronic modules or the transmission wires to the cloth or the heat melt adhesive film.

In the aforementioned cloth electronization product, the transmission wires are stitched to the cloth or the heat melt adhesive film, making use of the freezing stress, cementation, pressure or stretching force produced by the driving fit between the transmission wires and the cloth or the heat melt adhesive film, to connect the conductive regions in electronic modules and the transmission wires.

In the aforementioned cloth electronization product, the transmission wires are stitched to the cloth, making use of the pressure or the stretching force produced by the driving fit between the transmission wires and the cloth, to connect the conductive regions in electronic modules placed between the transmission wires and the cloth and the transmission wires. Meanwhile, because the packaging materials or the cloth for attire themselves have cracks, the electronic module itself and the conductive region are placed at different sides of the packaging materials or the cloth for attire. Therefore, a cloth is required on the top and at the bottom to complete the packaging of the entire electronic circuit.

In the aforementioned cloth electronization product, the transmission wires are woven on the cloth, and the transmission wires on one side of the cloth or on the heat melt adhesive film are dotted, so the conductive regions in an electronic module are covered by pulling out the dotted transmission wires from the cloth or the heat melt adhesive film.

In the aforementioned cloth electronization product, the transmission wires are knitted to the cloth or the heat melt adhesive film, so that the conductive regions in an electronic module are covered, by pulling the transmission wires out from the same points or close points on the cloth or the heat melt adhesive film, to form a circle.

In the aforementioned cloth electronization product, the transmission wires are first stitched to the cloth or the heat melt adhesive film, and the conductive regions of the electronic modules are placed on the transmission wires, and then the electronic modules, and the cloth or the heat melt adhesive film is stitched together using yarns, resulting in the transition between the conductive regions in electronic modules and the transmission wires.

In the aforementioned cloth electronization product, the conductive wires or the non-conductive wires are used to directly stitch the conductive regions in electronic modules and the transmission wires beneath it, to the cloth or the heat melt adhesive film, thus transiting the conductive regions and the transmission wires.

In the aforementioned cloth electronization product, the transmission wires are stitched to the cloth or the heat melt adhesive film. The transmission wires have multiple threads, so that they can cover up the conductive regions in an electronic module.

In the aforementioned cloth electronization product, the ways of covering up the conductive regions include covering up entirely or partially.

In the aforementioned cloth electronization product, the partial covering up can cover the top and the sides, the bottom and the sides, the front and the sides, or the back and the sides of the conductive regions in electronic modules.

In the aforementioned cloth electronization product, the transmission wires are stitched to the cloth or the heat melt adhesive film bordering the sides of the conductive regions, and the transmission wires clip or block the electronic modules, thus transiting both parties.

In the aforementioned cloth electronization product, there is Velcro on the cloth or the heat melt adhesive film, which fixes and transits the conductive regions in electronic modules and the transmission wires.

In the aforementioned cloth electronization product, the Velcro is conductive, so the conductive regions in the electronic modules do not have to directly contact the transmission wires.

In the aforementioned cloth electronization product, the transmission wires, which will pass through or come into contact with conductive silicone rubber, conductive rubber, conductive chips, conductive cloth such as silver fiber cloth, conductive bars such as stainless steel bars, or conductive multiple molecular materials, are stitched to the cloth or the heat melt adhesive film Meanwhile the conductive regions in the electronic modules or the transmission wires are either embedded or in touch with the conductive silicone rubber, conductive rubber, conductive chips, conductive cloth, conductive bars, or conductive multiple molecular materials.

In the aforementioned cloth electronization product, the transmission wires and the conductive regions in the electronic modules are connected by stapling on the cloth or the heat melt adhesive film.

In the aforementioned cloth electronization product, the stapler itself is conductive.

In the aforementioned cloth electronization product, the electronic modules and the transmission wires are on different sides of the cloth or the heat melt adhesive film.

In the aforementioned cloth electronization product, a backup transmission wire and the conductive regions in the electronic modules are connected.

In the aforementioned cloth electronization product, the backup transmission wire and the original transmission wire are on different sides of the cloth or the heat melt adhesive film.

In the aforementioned product of the cloth electronization, this method can be used as a pressure sensor or a pulling force sensor.

In the aforementioned cloth electronization product, the electronic modules are fixed by embedding them with insulators coating the transmission wires.

In the aforementioned cloth electronization product, the methods of transiting between the conductive regions in electronic modules and the transmission wires can also be used for the transition between the transmission wires or between the electronic modules.

The objectives and the technical problems of this invention are realized by using the following technical plans. Based on a method of electronizing the cloth proposed by this invention, the aforementioned cloth electronization products are produced.

This invention offers distinct advantages and benefits compared to the currently available techniques. Based on the aforementioned technical plans, the products and methods of the cloth electronization proposed by this invention at least possess the following advantages and beneficial effects: in the cloth electronization products made with this invention, the to transmission wires and electronic modules are "stitched" to the cloth or the heat melt adhesive film, while no welding is used on the cloth or the heat melt adhesive film, thus transiting the transmission wires or transiting the transmission wires and electronic modules. There are two methods: the first method is to "combine" electronic modules and the transmission wires first, then "stitch" them to the cloth or the heat melt adhesive film, while another method is to "stitch" the transmission wires to the cloth or the heat melt adhesive film, then connect the electronic modules and the transmission wires.

The methods above neither use welding on the cloth, nor are they restricted by different influences brought by different types of cloth. Meanwhile if the electronic modules or the transmission wires are found to have any problem, the system could detect it and, at the same time, replace the wire. More importantly, this method would simplify the process of electronizing the cloth, making it washable, and thus making its user feels comfortable. Meanwhile, surface mount devices that are traditionally used on the electronic circuit board, or the pin components, are fixed on the cloth, rendering an easy transformation of the cloth without changing the structures of the currently available textile, cloth, transmission wires, or electronic modules. This method uses the cloth or the heat melt adhesive film as an electronic circuit board and "stitches" electronic modules and the transmission wires to the packaging cloth or the heat melt adhesive film rather than having the electronic circuits integrally formed with the cloth for attire. The benefits of doing so are as follows:

1. The production doesn't require radical changes, and the production can be realized using the completely original textile or electronic equipment.

2. The quality of production can be controlled, and the cloth and electronic circuits are produced separately.

3. If a product has a problem, the packaging cloth on the electronic modules or the transmission wires can be changed directly, so as not to make the whole piece of clothing unusable.

4. The designs for products are flexible, and are not subject to the restraints posed by certain types of cloth.

The cloth or the heat melt adhesive film functions as the "soft" platform, the electronic modules are the "hard" modules, and the transmission wires and electronic modules can be "fixed" on the cloth or the heat melt adhesive film, staying effective under external forces. Meanwhile, the packaging cloth coating the electronic circuits guarantees insulation and freedom from external interferences. For example, electronic circuits can function normally even after experiencing twisting and pulling in a washer.

6. The users feel comfortable and do not have a sense of contact with a foreign body when using the cloth electronization.

7. If the signal produced has a problem, you can know which electronic module has failed and can replace it.

8. If the transmission wires get short-circuited or split open, it can be seen immediately.

As indicated by the points discussed above, this invention is about the products and methods for a type of cloth electronization. The cloth electronization product should consist of at least the cloth, one electronic module such as a resistance module, a microprocessor, a sensing module, etc., and at least one transmission wire connected to the conductive regions in the electronic modules. In this invention, electronic modules are first connected to the transmission wires, and then are stitched to the cloth, or the electronic modules and the transmission wires are connected in the process of stitching the wires to the cloth. The joints of electronic modules are connected to the transmission wires, and no welding is used during the process of stitching them to the cloth. Meanwhile, ways of stitching the transmission wires or electronic modules to the cloth can be plain weaving, knitting, tatting, embroidery and so on, or the circuits can be glued to heat melt adhesive film for packing and routing. Another invention is about the product and method of the cloth electronization. That cloth electronization product should have at least a cloth, at least one electronic module such as a resistance module, a microprocessor, a sensing module, etc., and at least one heat melt adhesive film as the electronic circuit board, as well as at least one transmission wire connected to the conductive regions in the electronic modules. In this invention, electronic modules are first fixed to the heat melt adhesive film to connect them, then they are merged into the packaging cloth or the cloth for attire; or the transmission wires are first fixed to the heat melt adhesive film to connect both parties, then both the heat melt adhesive film and the electronic modules are merged into the packaging cloth or the cloth for attire, as well as to the transit electronic modules and the transmission wires. The entire process uses no welding, while the methods of stitching the heat melt adhesive film and the transmission wires or electronic modules together can be plain weaving, knitting, tatting, embroidery, and so on, or the circuits can be glued to the heat melt adhesive film for packing and routing. With its obviously improved technology, and obvious positive effects, this invention indeed is an innovative, progressive, and practical new design.

The explanations above are only a summary of the technical plan for this invention. In order to more clearly understand the technical means used in this invention, so as to implement them, according to the contents of a user's manual, and to make this invention's objectives, characteristics and advantages, including those previously stated and all others, more obvious and more easily understandable, the following relatively better examples of implementation, complemented with illustrations, are explained in details, as follows.

BRIEF DESCRIPTION OF ILLUSTRATIONS

FIG. 5A to FIG. 5D illustrate the method of combining the transmission wires and electronic modules.

FIG. 26A and FIG. 26C illustrate the cloth loaded with the heat melt adhesive film electronic circuit board.

FIG. 36A and FIG. 36D illustrate the production equipment.

THE PREFERRED EMBODIMENTS

To further explain the technical means and the effects this invention has adopted to achieve its predetermined objectives of invention, a detailed explanation, complemented with illustrations and the relatively better examples of implementation, of the product and the method of the cloth electronization proposed in this invention and the specific ways of implementation, method, procedures, structures, characteristics and effects, is as follows.

What has explained about this invention and other technical contents, characteristics and effects will be clearly presented in the detailed explanation of the relatively better examples of implementation, illustrated in reference schemes. Via the explanation of specific method of implementation, a much deeper and more specific understanding of the technical means and the effects this invention has adopted to realize its predetermined objectives. However, the complementary illustrations only serve as references and explanations, and are not intended to restrict this invention.

Figure 1:
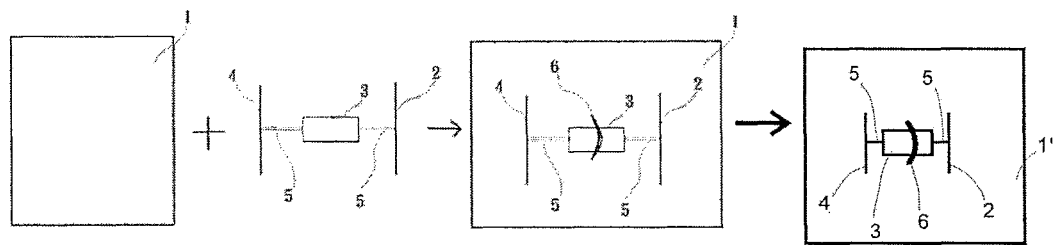
FIG. 1 illustrates the method of electronizing the cloth.
Figure 2:
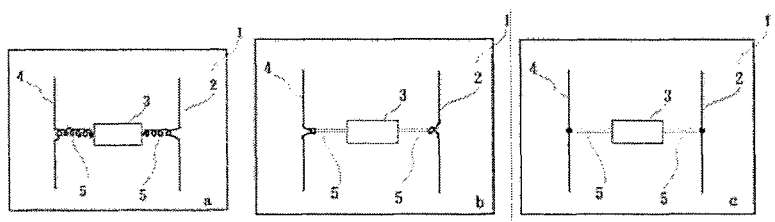
FIG. 2A to FIG. 2C illustrate how electronic modules and the transmission wires are connected.

The method of this invention is illustrated in FIG. 1, and FIG. 1 is the sketch map of the electronization of the cloth. Electronic module 3 like surface mount devices, or electronic modules with pins installed through holes (like the single-in-line model or dual-in-line model), is first connected to the transmission wires 2 and 4, which can be steel fiber, steel wire, copper wire, enamel wire, silver wire, wires mixed with gold, or organic conductive wires. The transmission wires 2 and 4 can be connected to the pins of electronic module 3, i.e. conductive region 5, through ways of twisting, knotting and point welding, as illustrated in FIG. 2A to FIG. 2C, FIG. 2A to FIG. 2C is the sketch map of connecting electronic modules and the transmission wires. Absolutely no tin is used in this process, then electronic module 3 is stitched to the packaging cloth 1, use various kinds of wires like yarn 6 to stitch electronic module 3 to the packaging cloth 1, and the methods of stitching can be plain weaving, knitting, tatting, embroidery, and so on. The packaging cloth 1 can be cotton, nylon, LYCRA® fiber, plastic linen and other materials, and the method of weave for the packaging cloth will not influence the process in which electronic modules and the transmission wires are fixed to the packaging cloth. In addition, to enhance the reliability of the fixation of the electronic modules, the transmission wires and the cloth, the transmission wires and electronic modules, after being combined, can be fixed by "gluing", for example, the heat melt adhesive film or the heat-shrinkable sleeve, so as to make the connection between electronic module's pin 5 and the transmission wire 2 or 4 more stable, and at the same time, insulated. The next step is to stitch or glue the cloth electronizalion, like a mesh belt, to the cloth for attire, to complete the electronization of the cloth product.

Figure 3:
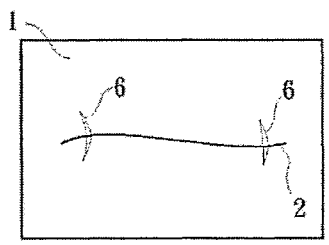
FIG. 3 illustrates how the transmission wires are fixed to the cloth.

In this method, the cloth electronization mainly uses non-conductive wire such as yarn 6 to stitch electronic module 3 to the packaging cloth 1. Moreover, rather than using the way of stitching the yarn, electronic modules can be directly used to "glue", onto the packaging cloth. As to the transmission wires, they can be stitched to or glued to the cloth, and the ways of stitching can be further divided into: the transmission wires themselves stitch into the cloth 1, or use conductive or non-conductive wires like yarn 6 to stitch the transmission wire 2, as illustrated in FIG. 3, and FIG. 3 is the sketch maps of fixing the transmission wires to the cloth.

Figure 4:
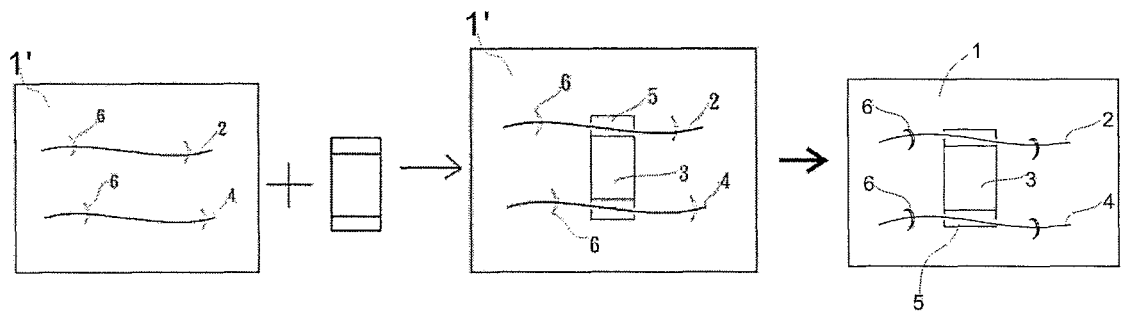
FIG. 4 illustrates the electronization of the cloth.
Figure 5A:
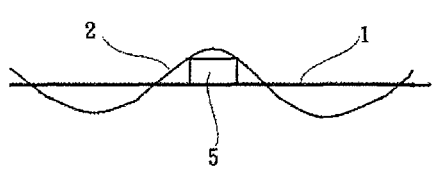
Figure 5B:
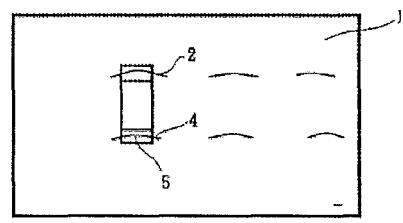
Figure 5C:
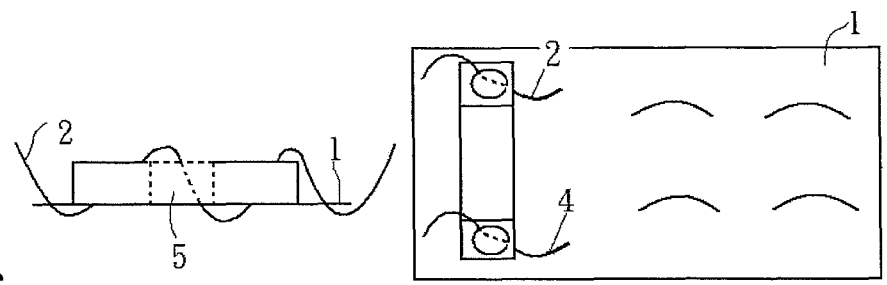

Another method in this invention is as illustrated in FIG. 4, and FIG. 4 is the sketch map of the cloth electronization. In this process, the transmission wires 2 and 4 are first stitched to the cloth for attire 1'1. This process can be completed by the transmission wire "stitching" itself to the cloth for attire or, stitching non-conductive materials like yarn 6 to the cloth for attire 1', and then connecting the conductive regions 5 in electronic modules 3 and the transmission wires. The methods of stitching the transmission wires to the cloth for attire 1' can be plain weaving, knitting, tatting, embroidery, and so on, while the connection between the conductive region 5 in electronic module 3 and the transmission wires 2 and 4 may use the tension or the pressure from the sewing up between the cloth for attire 1'1 and the transmission wire 2, as illustrated in FIG. 5A to FIG. 5B, and FIG. 5A to FIG. 5B are the sketch maps of combining the transmission wires and electronic modules. That is to say, embed the conductive region 5 in an electric module into somewhere between the transmission wire 2 and the cloth for attire 1', the pressure or the tension coming from sewing up the transmission wire 2 and the cloth for attire 1' is used to fix the conductive region 5 in electronic modules and to connect the transmission wires. To fix the conductive region 5 in electronic modules and to connect it with the transmission wires, and then stitch or glue the packaging cloth 1 to the cloth for attire 1' to complete the cloth electronization product.

Figure 6:
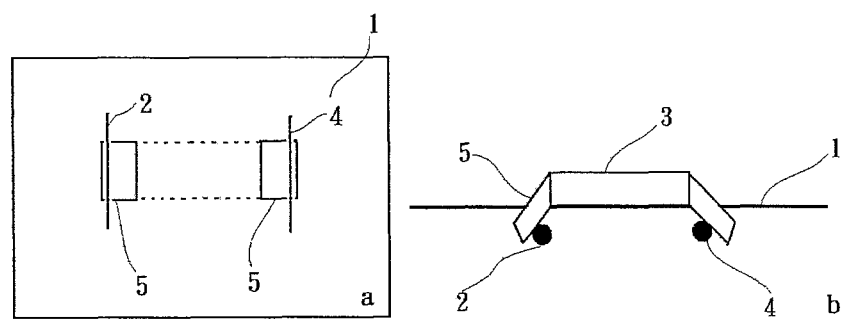
FIG. 6A to FIG. 6B illustrate another way of combining the transmission wires and electronic modules.

Another type of transformation involves the packaging cloth or the cloth for attire 1 that has cracks in itself, so electronic module 3 is placed on one side of the packaging cloth or the cloth for attire, while the conductive regions are exposed from the cracks on the other side of the packaging cloth or the cloth for attire 1, to connect the transmission wires, as illustrated in FIG. 6A to FIG. 6B. FIG. 6A to FIG. 6B are the sketch maps of another way of connecting the transmission wires and electronic modules. If the conductive region 5 in electronic module 3, as illustrated above, has pins, it can be further fixed by knotting or inter-wreathing the transmission wires. All the same the heat melt adhesive film or the heat-shrinkable sleeve can be used for insulation.

Figure 7:
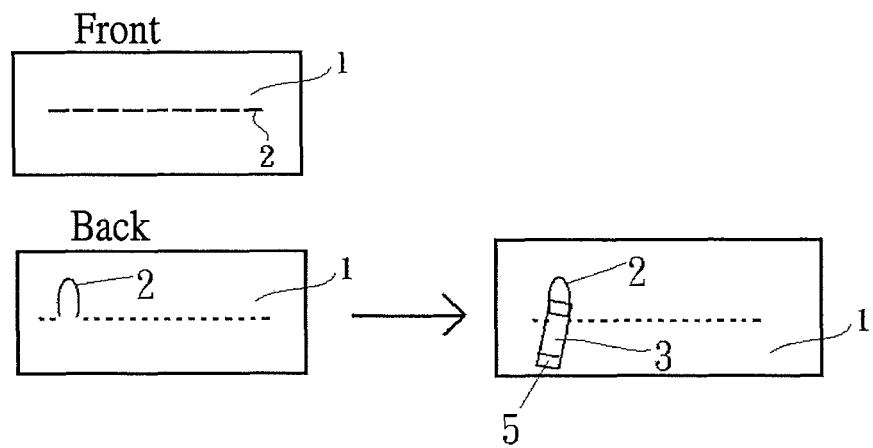
FIG. 7 illustrates the method of plain weaving the transmission wires.
Figure 8:
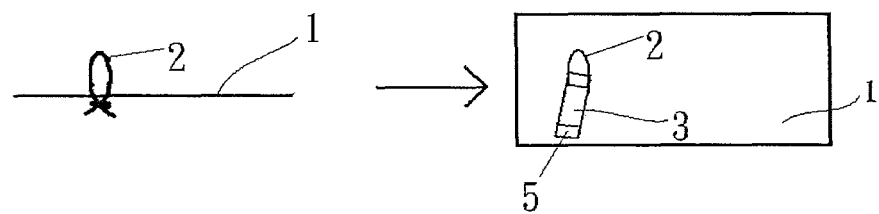
FIG. 8 illustrates the way of connecting the transmission wires and the conductive regions in the electronic modules.

Another way is to use transmission wires 2 and 4 to "entrap" the conductive region 5 in electronic module 3, as illustrated in FIG. 7. FIG. 7 is the sketch map of the plain weaving of the transmission wires, and that of weaving the transmission wire 2 on the packaging cloth or the cloth for attire, the upper wire being the transmission wire 2 and the lower wire being the non-conductive wire like the yarn. The side with many transmission wires is on the front, while the side with many dotted transmission wires is on the back. We pull the dotted transmission wires on the back from the surface of the cloth 1 to show them "in a circular shape", which "entraps" the conductive region 5 in electronic module 3. In this way the transmission wires mainly run on one side of the packaging cloth or the cloth for attire, while electronic modules are placed on the other side of packaging cloth or the cloth for attire. To synthesize the methods mentioned above, both the upper and the lower sides of the same to transmission wire can be connected to electronic modules. Of course in conditions where the electronic modules have pins, the electronic modules can be fixed by knotting or inter-weaving the transmission wires. Similarly, the method of knitting can be used to allow electronic modules to pass through the same point or two close points on the cloth 1, as illustrated in FIG. 8. FIG. 8 is the sketch map of connecting the transmission wires and the conductive regions, and the same effects of "entrapping" electronic modules can also be produced. After entrapping electronic module 3, the transmission wire 2 further knots, inter-wreathes or glues to produce a more stable effect.

Figure 9:
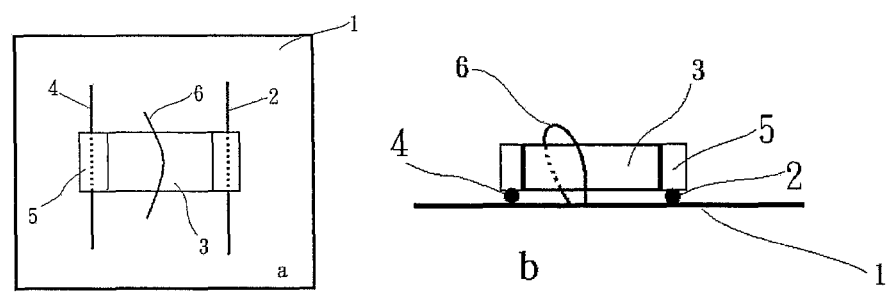
FIG. 9A to FIG. 9B illustrate the ways of connecting the transmission wires and the conductive regions in the electronic modules.

Another method uses yarn 6 to stitch electronic module 3 to the packaging cloth or the cloth for attire 1, thus connecting the conductive region 5 in electronic module 3 and the transmission wires 2 or 4, as illustrated in FIG. 9A to FIG. 9B. FIG. 9A to FIG. 9B are sketch maps of connecting the transmission wires and the conductive regions. That is to say, the fixation of electronic module 3 and the cloth 1 can connect the transmission wire 2 and the conductive region 5. Another method is to directly stitch the conductive region 5 and the transmission wire 2 together if the conductive wires were stainless steel wires or silver yarns. This method is the most suitable for electronic modules with pins. Of course, the same effects can be achieved when the non-conductive yarns are used to directly stitch the conductive region 5 to the transmission wire 2 together.

Figure 10:
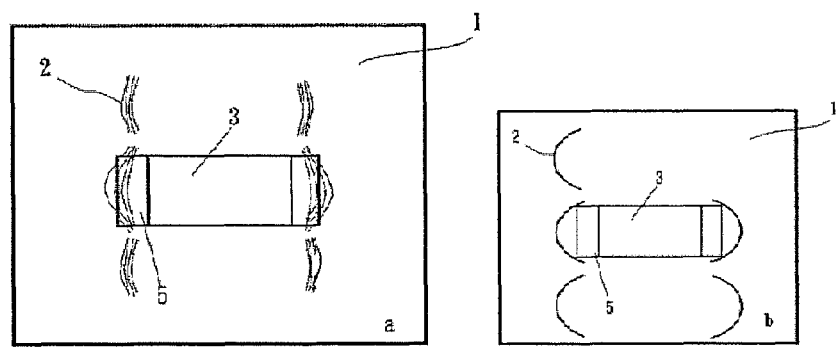
FIG. 10A and FIG. 10B illustrate the first relatively better examples of implementation for the connection between the transmission wires and the conductive regions.

Another method is that when the transmission wires are stitched to the cloth 1, the transmission wires have multiple threads so that they can entrap the conductive region 5 in electronic module. The ways of entrapping include all-encompassing entrapping, partial entrapping, for example, partially entrap the top and the side, the bottom and the side, the front and the side, the back and the side of the conductive regions, or only the conductive regions on the side and the transmission wires are clipped, forming conditions like all-encompassing entrapping or partial entrapping on the top and on the side, as illustrated in FIG. 10A. If the transmission wires have multiple threads or a single thread, just clip or block an electronic module on its side to transit both parties, as illustrated in FIG. 10B. FIG. 10A to FIG. 10B are the sketch maps of the first relatively better example of implementation of connecting the transmission wires and the conductive regions.

Figure 11:
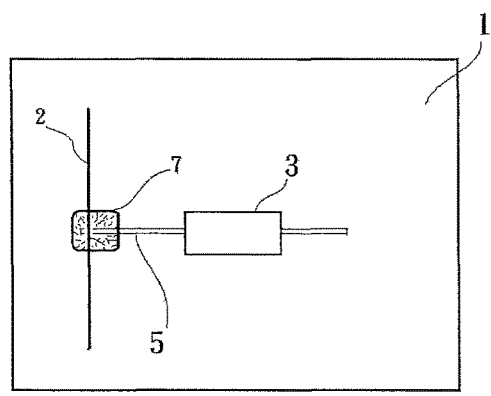
FIG. 11 illustrates the second relatively better example of implementation of the connection between the transmission wires and the conductive regions.

Another method is to stitch a Velcro 7 (loop) to the packaging cloth or the cloth for attire, to replace the original yarn 6, to fix electronic module 3 and the transmission wire 2, so the conductive regions in electronic modules are connected to the transmission wires, as illustrated in FIG. 11, and FIG. 11 is the sketch map of the second relatively better example of implementation of the connection between the transmission wires and the conductive regions. In addition, a Velcro (hook) (not shown in the illustration) can be added to seal up Velcro 7, so as to make it more difficult to move the conductive region 5 and the transmission wire 2. If Velcro 7 (loop) or the Velcro (hook) added were also conductive, it would be more effective in making the conductive region 5 and the transmission wire 2 not to move. At this time, Velcro 7 (loop) or the Velcro (hook) added only come into contact with the conductive region 5 in electronic module 3.

Figure 12:
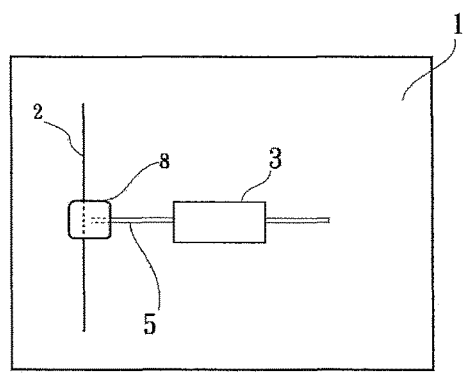
FIG. 12 illustrates the third relatively better example of implementation of the connection between the transmission wires and the conductive regions.

Another method is to stitch the transmission wire 2 to the packaging cloth or the cloth for attire 1, after passing through or coming into contact with a conductive silicone rubber, conductive multi-molecular cloth, conductive bars or conductive rubber 8, then embed or make the conductive region 5 in electronic module 3 contact conductive silicone rubber or rubber 8, as illustrated in FIG. 12, and FIG. 12 is the sketch map of the third relatively better example of implementation of connecting the transmission wires and the conductive regions.

Figure 13:
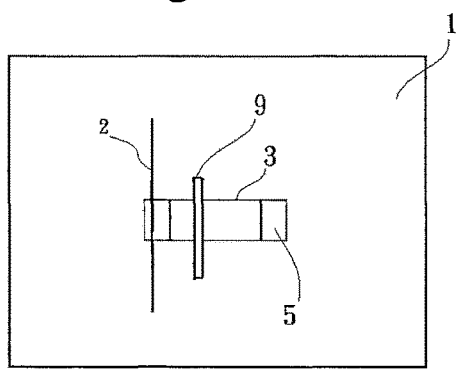
FIG. 13 illustrates the forth relatively better example of implementation of the connection between the transmission wires and the conductive regions.
Figure 14:
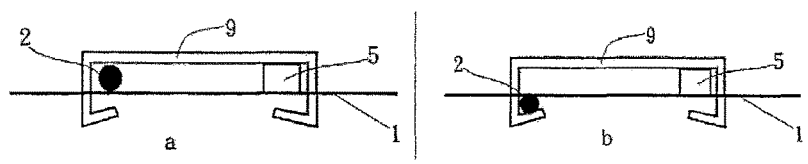
FIG. 14A and FIG. 14B illustrate the method of connecting the transmission wires and the conductive regions.
Figure 15:
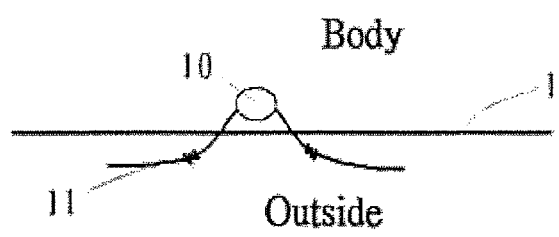
FIG. 15A and FIG. 15E illustrate the method of connecting the transmission wires and the conductive regions.

The method of "stapling 9" can be used to connect another transmission wire 2 and electronic module 3, use stapler 9 to replace yarn 6 for fixation. At that time the "stapler" can be non-conductive material, as illustrated in FIG. 13, and FIG. 13 is the sketch map of the forth relatively better example of implementation for connecting the transmission wires and the conductive regions. If conductive materials like the stainless steel are used, then connect the transmission wire 2 and the conductive region 5 in electronic module 3, as illustrated in FIG. 14A, on one hand, and electronic module 3 and the transmission wire 2 can also be stitched to the packaging cloth or the cloth for attire, on the other hand. As illustrated in FIG. 14B, one stapler can also connect to multiple electronic modules or multiple transmission wires, and FIG. 14A to FIG. 14B are the sketch maps of connecting the transmission wires and the conductive regions.

All the methods mentioned above are interchangeable. For example, the conductive silicone rubber or rubber 8 and electronic module 3 and the transmission wire 2 can be combined first, and then stitched to the packaging cloth or the cloth for attire 1, meanwhile the transmission wire 2 can have various ways of connecting to various kinds of electronic modules 3. For the same reason, replace "electronic modules" with another "transmission wire" to connect various transmission wires, for example, only knot and twist . . . two transmission wires at crossings to connect two transmission wires in a "T" shape. That is to say, the various ways of connecting "the conductive regions" and the transmission wires are just the way of connecting another transmission wire and the original transmission wire.

For the same reason, the way of connecting the transmission wire 2 and electronic module 3 can be used to connect one electronic module with another; for example, ways of connection in a "T" shape stand for knotting, inter-wreathing, and so on among three electronic modules. Two electronic modules are combined using a way of connection in an "L" shape, and then another conductive region 5 in every electronic module is combined with the transmission wire 2. In the methods mentioned above, the packaging cloth or the cloth for attire can be replaced by the heat melt adhesive film. Do as follows: place the electronic circuits on the heat melt adhesive film to form an electronic circuit board, then merge the heat melt adhesive film into the packaging cloth or the attire for packing and insulation; meanwhile, this electronic circuit merged into the cloth does not show its original structure and depth, producing a minimized effect.

Figure 16:
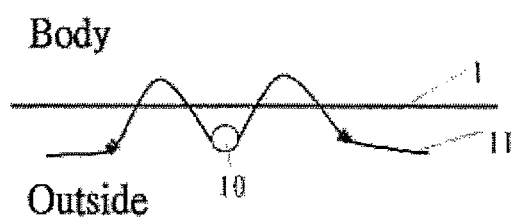
FIG. 16A and FIG. 16B illustrate another method of stitching the thermal resistance and the enamel wire to the cloth.

The following are a few examples of relevant applications, the first being a Temperature Coat. We put each pin of 10 Heat Resistance, which are interwoven with conductive region 5 and the enamel wire 11, on the front, the back, the left and the right of a coat. Moreover, the Heat Resistance of 10 is placed on the inner side of the coat, and pin 5 passes through cloth 1 to form a knot with the enamel wire 11. This cloth, on which there is a packaging cloth for packing and insulation, as well as for protecting the Heat Resistance and the enamel wire, measures a person's body temperature. This is shown in FIG. 16A, where FIG. 16A is the sketch map for stitching the Heat Resistance and the enamel wire to the cloth. In particular, during sleep, a Heat Resistance is bound to be pressed under your body, and the temperature measured is the body temperature. If a Heat Resistance of 10 is placed outside, it can measure the temperature in the outside environment, as illustrated in FIG. 16. FIG. 16 is another way of stitching the Heat Resistance and the enamel wire to the cloth. If every Heat Resistance of 10 is connected to a capacitive C 1, C 2, C 3, C 4 and an inductance L 1, L 2, L 3, L 4, as shown in FIG. 17, series capacitor inductance and resistance yield to a resonance circuit, whose resonance frequency is $$f = \frac{1}{2\pi\sqrt{LC}}.$$

Communicative signals are put in at both ends. When the frequency of communicative signals is very close to f, their resistance is close to zero, and the current can smoothly pass capacitance and inductance. On the contrary, when the distance between the frequency of communicative signals and f is very great, the resistance is very great, and it's hard for the current to pass capacitance and inductance, as well as the series resistance.

Figure 17:
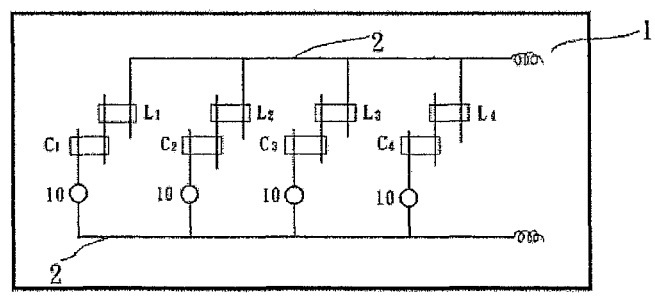
FIG. 17 is the sketch map of the temperature coat.

In FIG. 17, we can choose different values of Inductance and Capacitance to make the corresponding resonance frequency to vary greatly (more than 10 times), then we can use communicative signals of varying frequencies to measure different Heat Resistance separately, so as to make multiple Heat Resistances share two output points. In addition, these 2 output lines spiral a distance first, during this distance a conductive magnetic material like a magnetic bar can be used to prevent the interferences of the EMI, and FIG. 17 is the sketch map of the electronic circuit of the temperature coat. If a user sits on a thermal resistor attached to his or her pants, his or her anus body temperature can be measured. In short, the cloth for attires mentioned above are all equipped with a packaging cloth.

Figure 18:
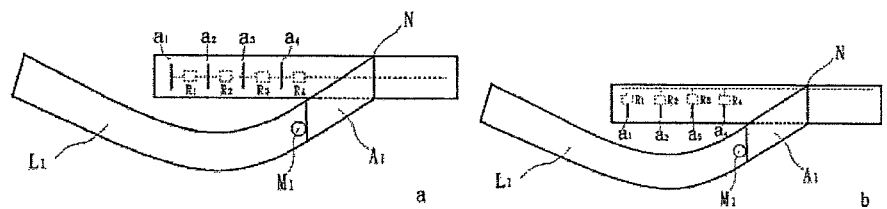
FIG. 18A and FIG. 18B illustrate a numeric respiration detection belt.
Figure 19:
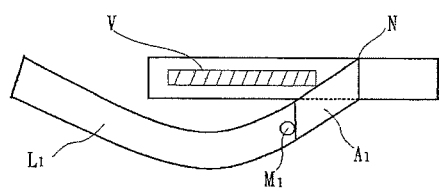
FIG. 19 illustrates a mockery respiration detection belt.

Example 2 is the detection done by a respiration detection belt. First of all, overlap two respiration bands, and combine the same ends N of both bands together, one of which is an elastic band A1 and the other is a non-elastic cloth of length L1. A conductive material like a Convex clasp M 1 is placed on one band, and four conductive wires a 1, a 2, a 3, a 4 are placed on the other band that is not elastic. When a user's stomach or chest becomes bigger while inhaling air, the elastic band A1 becomes longer, leading the conductive materials M 1 to move, but at this time, a 1, a 2, a 3, a 4 conductive wires remain unmoved, leading the Convex clasp M 1 to come to various contact with a 1, a 2, a 3, a 4 conductive wires, in response to the respiration. So the frequency and amplitude of the respiration that we measured, as FIG. 18A illustrates, are four conductive wires each stringing a resistor R 1, R 2, R 3, R 4. As shown in FIG. 18B, four conductive wires each form their parallel resistors R 1, R 2, R 3, R 4, and of course each resistor R can be replaced by capacitance C or inductive L or other electronic modules, such as a diode. In addition, we can also provide one conductive material such as 10 ohms K, or the conductive silicone rubber V, then the changes in resistance can be measured because of Convex clasp M 1's shifting of positions while breathing in and out air, as illustrated in FIG. 19, and FIG. 19 is the sketch map of a mock respiration belt. We can also have more than one Convex clasps, like two Convex clasps. The distance between both clasps is greater than the lengths of the four conductive wires a 1, a 2, a 3 and a 4 or the length of the conductive material V, so one of these two Convex clasps is bound to interact with the other conductive wire or the conductive material V. FIG. 18 A to FIG. 18B are the sketch maps of a numeric respiration detection belt.

Figure 20:
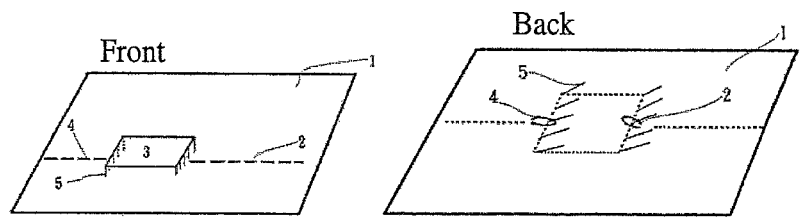
FIG. 20 illustrates the way of connecting processors.

An average electronic circuit commonly uses electronic modules with three pins, such as transistors, gates and so on, so there are three conductive regions. We can connect a conductive region and the transmission wires of a circuit on one side of the packaging cloth or the cloth for attire, while the other two conductive regions and the transmission wires come into contact on the opposite side of the packaging cloth or the cloth for attire, so as to avoid dangers of fusion due to overlapping. In addition, processors with 8 pins or 16 pins may use the method of "entrapping" the transmission wires, that is to say, pins, i.e. the conductive regions, pass through the cloth to hook up the transmission wires, then every transmission wire won't have the chance to contact another transmission wire that is connected with another pin, as illustrated in FIG. 20, and FIG. 20 is the sketch map of connecting the processors. If there is a need, the adjacent transmission wires are "on the top and on the bottom"—that is, the transmission wires connected to the first pin are on one side of the packaging cloth or the attire, while the transmission wires connected to the second pin are on the other side of the packaging cloth or the attire, so that there won't be any possibility of a short circuit.

Figure 21:
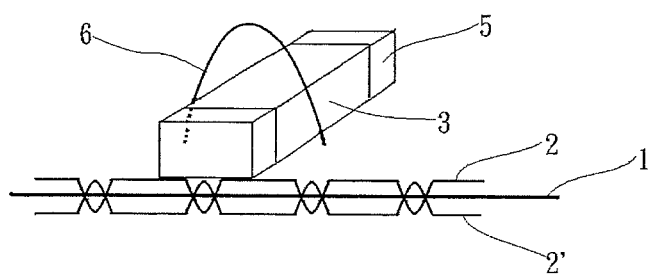
FIG. 21 illustrates the way of connecting the transmission wires and the conductive regions.
Figure 22:
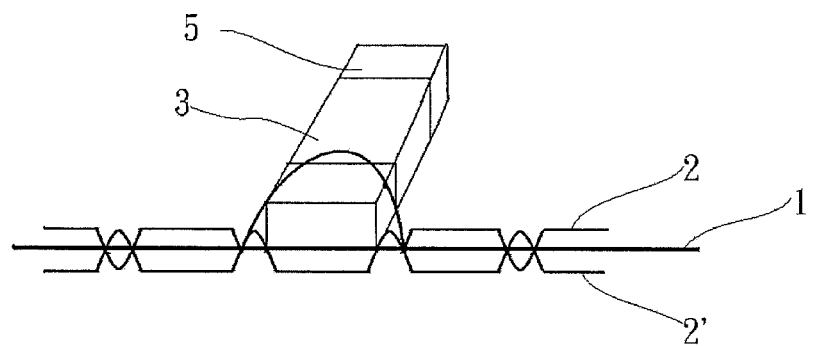
FIG. 22 illustrates another way of connecting the transmission wires and the conductive regions.

Additionally, it can also have standby transmission line 2'. When the transmission line 2 is cut off, the whole circuit can still be in operation as the conduction region 5 of electronic component 3 is connected with another transmission line 2' simultaneously, as in FIG. 21. FIG. 21 is the diagrammatic sketch on connection method of standby transmission line and conductive region. Identically, if the transmission line 2 has short circuit with other transmission line 4, the standby transmission line 2' is in operation, as standby transmission line 2' is on the other side of cloth 1 i.e. it is on different side with transmission line 2, as in FIG. 22. FIG. 22 is a diagrammatic sketch for another connection method involving a standby transmission line and conductive region.

Figure 23:
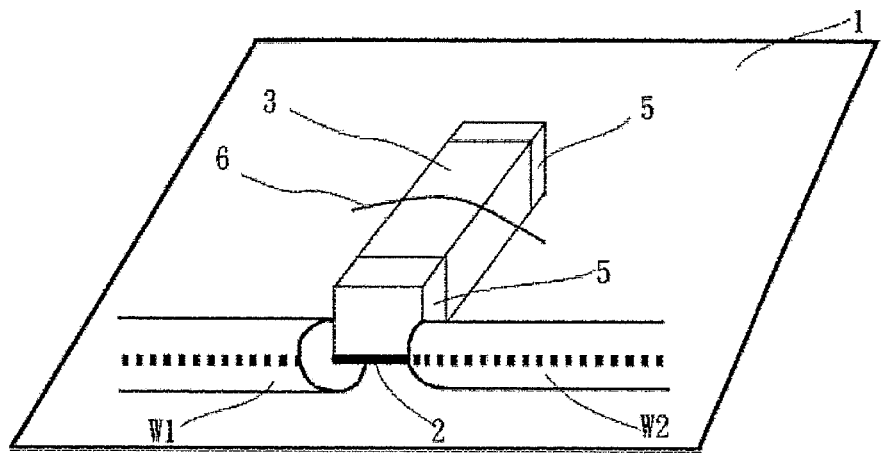
FIG. 23 illustrates the way of connecting the transmission wires and the conductive regions.

Commonly-used transmission lines have multiple types, such as twin-lead wire, parallel multi-conductor, coaxial wire, ribbon line, single-core wire, multi-core and multiple strands etc. Many transmission lines have insulator outside of the conductor, such as Teflon, PVC or other polymer materials as insulator, as in FIG. 23. FIG. 23 is a diagrammatic sketch for a connection method involving a transmission line and conductive region. When the conductive region 5 of electronic component 3 is connected with transmission line 2, it needs eliminating the outer insulator W. If the distance between two insulators W1 and W2 of transmission line 2 is just near the width of electronic component, place the electronic component 3 on the transmission line 2 and it is just embedded in the insulators W1 and W2 and is not easy to be moved, as in FIG. 23. As the insulators W1 and W2 have elasticity and toughness themselves, insulators W1 and W2 can be fixed and connected with the conductive region of electronic component due to transmission line is sewn on the cloth 1. At the moment, electronic component 3 is just under the transmission line 2. If the electronic component 3 is above the transmission line 2, another yarn 6 is fixed on the cloth 1, as in FIG. 23.

As the invention is to sew electronic component 3 or transmission line 2 on the packaging cloth 1 or clothing cloth 1', it will affect the output results whether the conductive region 5 of electronic component is connected with the transmission line 2 closely. Therefore, we use this method to generate pressure or tension sensor, i.e. the output value is varied as the variation of external pressure or tension when the conductive region of electronic component is connected with the transmission line 2, e.g. if the electronic components are resistors, capacitors, inductors, amplifiers, switches, thermistors, microphone and electrodes etc, the output value may have different results due to the closing degree of conductive region and transmission line 2, and the closing degree may produce variation as the changing of external pressure or tension. Therefore, it can be pressure or tension sensor.

Additionally, to increase pressure or tension sensor value, we can add non-conductive yarns or materials between the conductive region of electronic component and transmission line to increase the sensing value of pressure or tension sensor. For above stated all kinds of methods, weaving, knitting, crocheting, knotting, stitching and other methods are used for sewing and pasting between the transmission line and cloth. The routing methods can be divided into straitening, bending, snake-like shape, above or below different cloth layers or the same cloth layer, and other methods.

Finally, if the packaging cloth 1 or clothing cloth 1' has integrated transmission line originally, it can be used as standby transmission line 2'. In one word, the electronic component and transmission line of the invention are added on the packaging cloth 1 or clothing cloth 1' additionally. Therefore, when the electronic component 3 or transmission line 2 has failure, it is permitted to remove the electronic component 3 or transmission line 2 and replace them with new ones. It is unnecessary to discharge them completely and the user can make recovery independently.

Additionally, to enhance the fixing reliability of electronic component, transmission line and cloth, it can glue again for fixing after the combination of transmission line electronic component, such as adhesive or heat shrink tubing. In this way, it enables the jointing of pins of electronic component and transmission line 2 or 4 more stable and has insulation at the same time.

For the above methods, we use avometer, oscilloscopes and other electronic equipment to measure whether the electronic component is in good contact with the conductive region of transmission line. At the same time, it measures whether changes are produced under the effect of external force, thus to adjust the relations between the electronic component and transmission line or between the electronic component and another electronic component or between the two transmission lines, for example, shorten the distance between the two transmission lines to increase the force of two transmission line to the electronic component, or the cloth itself has elasticity, or add elastic material on the cloth, such as SBR, sponge and rubber etc. In this way, it enables the electronic component be fitter to the conductive region of transmission line. If the transmission line or the electronic component itself has elastic characteristics, it may generate better closing effect when the partial insulation layer eliminated transmission is jointed with the conductive region of conductive component, for example, the external insulation layer of transmission line is composed of elastic materials, On the other hand, when the conductive region of electronic component or the surface of transmission line is not smooth, it is also difficult to be separated for jointing of both, for example, the surface of conductive region of electronic component is in concave shape, concave structure is embedded when the transmission is jointed with the conductive region, which may lead to stable combination of the both.

Another method of the invention is to use the heat melt adhesive film as the substrate, and at least one conductive region of electronic component or at least one transmission line is sewn, stuck or pasted on the heat melt adhesive film to form a circuit board. In the method of taking another heat melt adhesive film as the substrate, it is changed into fixing the heat melt adhesive film on the cloth for use as the substrate, and at least one electronic component or at least one transmission line is stuck or pasted on the heat melt adhesive film on the cloth to form a circuit board. Transmission lines on the heat melt adhesive film can be conductive fabric, conductive strips, stainless steel wire, conductive wire, silver fiber, polymer conductive material and rubber coated wire and enameled wire etc. If it has insulation layer, such as rubber coated wire, it can use chemical or mechanical method to eliminate the insulation layer on the connector of conductive region to contact the electronic component.

Figure 24A:
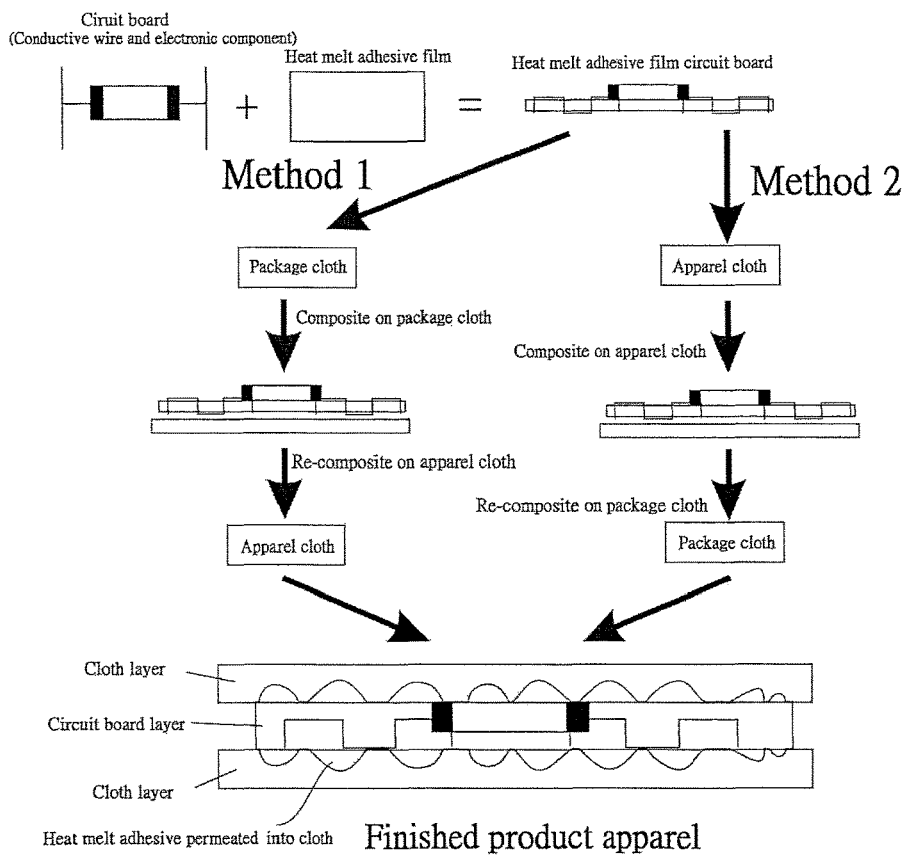
FIG. 24A and FIG. 24B illustrate the overall architecture diagram for traditional textile products complemented with the electronic circuit board whose basis is the heat melt adhesive film.
Figure 24B:
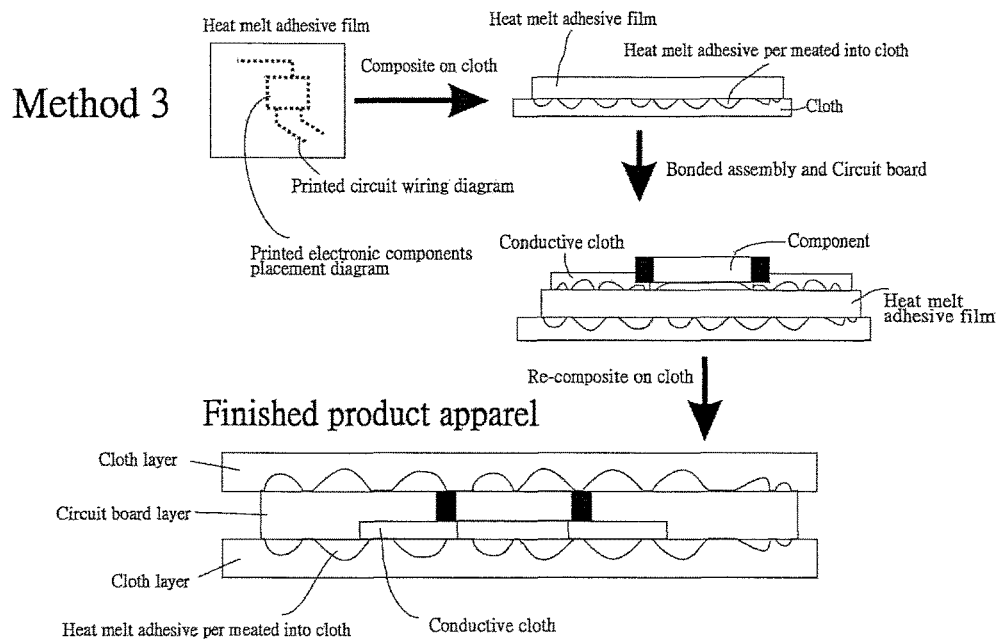

As in FIG. 24A to FIG. 24B, FIG. 24A to FIG. 24B are general structure diagrammatic sketches of installing manufacturing circuit board taking hot melt film as substrate on traditional fabrics. The electronic product of the cloth shall have at least a piece of cloth, at least an electronic component, such as resistor, microprocessors and sensing assembly etc., and at least one hot melt film as a substrate. At the same time, it shall have at least one transmission line to be connected with the conductive region of electronic component. The invention is to fix the electronic component and transmission line on the heat melt adhesive film first to join them both, and then to integrate them into the packaging cloth (as in Method I of FIG. 24A) or clothing cloth (s in Method II of FIG. 24A). During the whole process, it does not need welding. At the same time, sewing methods of the heat melt adhesive film and transmission line or electronic component are weaving, knitting, tatting or embroidering, or it is used jointing method to complete stamping and routing, packaging process of electronic component which uses the heat melt adhesive film as a circuit board. It uses the heat melt adhesive film as a substrate to manufacture the circuit board, and then adds it to the traditional fabrics. It can combine with the packaging cloth and take re-combination with the clothing cloth (it can also be completed by sewing, sticking or pasting) (as in Method I of FIG. 24A), or the sequences can be reversed. In another method, the heat melt adhesive film is combined with clothing cloth first, and electronic components and transmission lines are fixed on the heat melt adhesive film, and then recombine the packaging cloth on it (as in FIG. 24B). The process of packaging cloth is unnecessary. The sequence can be reversed.

In the cloth electronization method of the invention, a circuit routing layout of the circuit board can be printed on the heat melt adhesive film by heat transfer process and ink jetting method. Then sew, stick or paste the transmission lines on the heat melt adhesive film along the routing plan. Or it uses computerized sewing machine to sew a pre-arranged routing plan on to the heat melt adhesive film directly.

First, print a circuit routing plan and electronic component placement drawing on the heat melt adhesive film. Then combine it with the cloth, and use heat gun to heat and use conductive cloth (other plain conductor or insulation line with degumming on contact point) as the transmission conductors of circuit. Finally, recombine it with the cloth (it can also be completed by sewing, sticking, or pasting) so that the heat melt adhesive film is placed between two layers of cloth and is not exposed to complete the complete stamping and routing, packaging process of electronic component which takes the heat melt adhesive film as circuit board.

In another implementation example of the invention using heat melt adhesive film as the circuit board, the circuit board is a heat melt adhesive film with a transmission line. It is placed on the electronic component to enable the conductive region of electronic component contact with the conductive region of transmission line. Then, take heating and fixing to produce electronic board with contacting of electronic component and transmission line. During the process, a heat melt adhesive film without a transmission line can be added to increase the insulation of the electronic board. Additionally, if contact between the electronic component and transmission line is required, make the two installed heat melt adhesive films have transmission lines during the generation process of the circuit board. Place an electronic component between the two films to enable the conductive region of electronic component contact with the conductive region of transmission line. Finally, use heating and fixing to stick, paste, or sew the two heat melt adhesive films, so that the produced circuit board can enhance conduction intensity of transmission line and the electronic component.

Figure 25A:
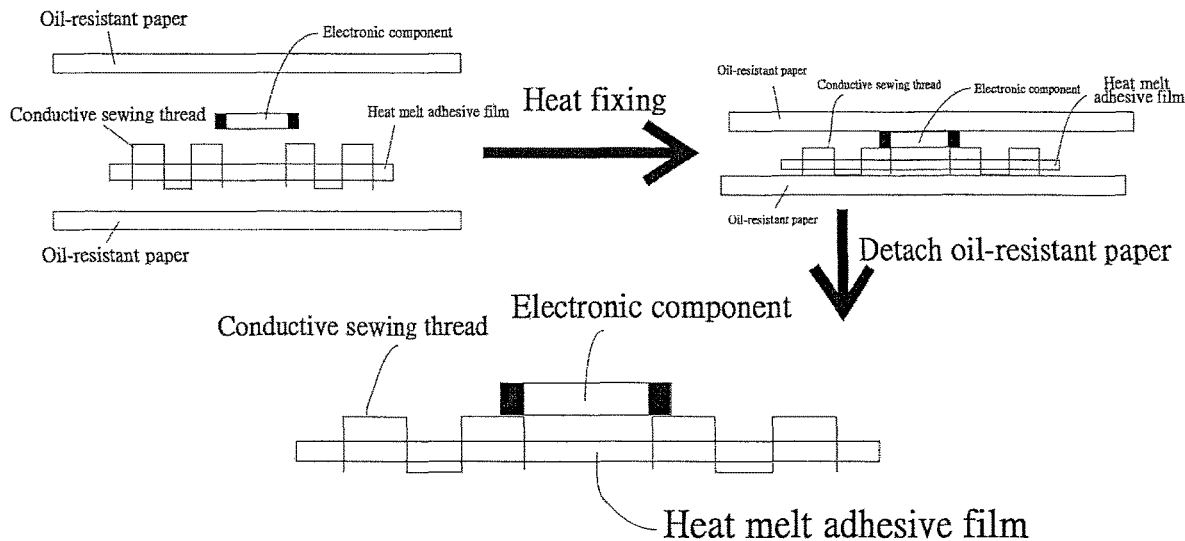
FIG. 25A and FIG. 25C illustrate the production of the heat melt adhesive film electronic circuit board, with the transmission wires and electronic modules fixed on the heat melt adhesive film.
Figures 25B, 25C:
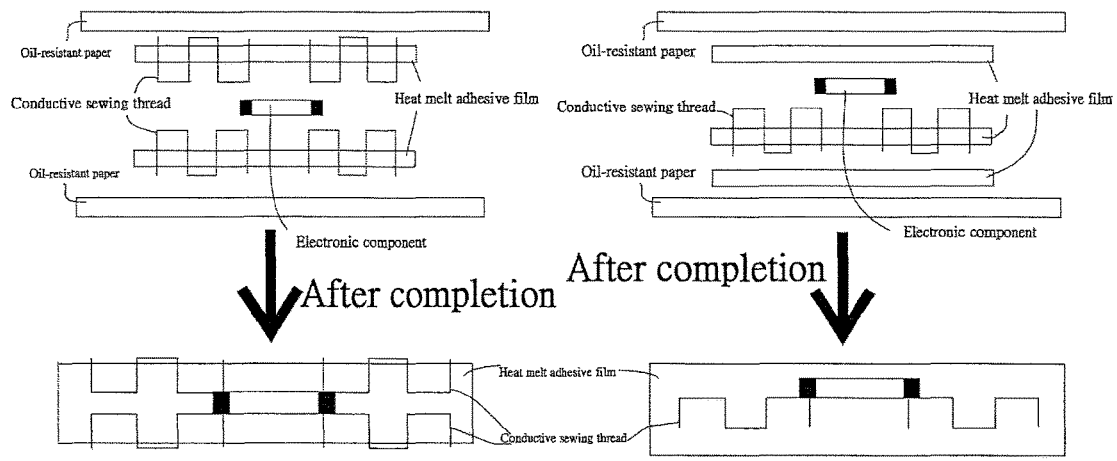

The method of fixing electronic component and transmission line on heat melt adhesive film (as in FIG. 25A) is to use sewing thread (or conductive cloth or insulated conductive wires etc.) to produce circuit board taking the hot melt film as substrate. When the conductive sewing thread is used, it can use computerized pattern machine directly to install pre-arranged routing plan on heat melt adhesive film by direct sewing method to form heat melt adhesive film PCB. Then use gang drilling machine to place electronic components on corresponding position to achieve heat melt adhesive film PCBA. If conductive cloth is used, print conductor routing plan on threading position in advance, then use heat gun, high frequency, ultrasonic or heat press machine, infrared heating method and other heating tools to melt partial film. Then arrange conductors manually along the printed conductor routing plan. If the used insulation conductor needs eliminating insulation layer in the component compression jointing position to bare the conductor, use gang drilling machine to place electronic components on corresponding positions. Pad oil separation paper above and below. Take heating to melt the heat melt adhesive film slightly. Splice the previously placed electronic component and conductor on the heat melt adhesive film. Finally, remove the upper and lower oil separation paper (as in FIG. 25A). Additionally, if better contacting between the electronic component and conductor is required, one layer or two layers of conductors can be used to increase conductor compressing surface and compress the electronic component and conductor to obtain better contacting (FIG. 25B). Furthermore, if the electronic component has higher requirements for packaging and insulation environment, it can add another layer of hot melt film above or below to improve overall circuit packaging and insulation properties (FIG. 25C).

I. Performance Characteristics of hot melt adhesive film are as the following:
  1. Have excellent adhesion to various types of textiles
  2. Washable, dry-cleaning available, easy to use and efficient
  3. Without pollution to human body and environment II. Types of hot melt adhesive film are as the following:
  1. For high-end products: Polyamide hot melt adhesive film (PA), polyester hot melt adhesive film (PET), polyurethane hot melt adhesive film (PU)
  2. For common products: Polyolefin hot melt adhesive film (PO), ethylene-vinyl acetate copolymer hot melt adhesive film (EVA)

III. Features of all kinds of hot melt adhesive film are as the following:
  1. PA, PET, PU hot melt adhesive films have excellent temperature resistance performance and strong bonding strength.
  2. PET melt hot melt adhesive film has excellent washing resistance performance.
  3. PA hot melt adhesive film has excellent to dry cleaning resistance performance.
  4. PU hot melt adhesive film is suitable for leather and PVC classes.

TABLE 1

| | Film Name | | | | |
|---|---|---|---|---|---|
| Process Parameters | EVA | PA | PET | PU | PO |
| Temperature ° C. | 80-120 | 120-200 | 130-200 | 120-200 | 100-200 |

Notes:

a. The above is only for reference. As different stuck materials, different environment and other factors, different process conditions can be selected. It can take experiments first to confirm the best process condition. Relationship among temperature, pressure and time can be conversed appropriately according to the condition.

b. Besides hot-pressing process, it can also spread hot melt adhesive film on adherend to heat to the melting temperature. Then overlap the sticking surface of the other adherend, and apply proper pressure, cooling and solidification to complete bonding.

c. Heating tool or heating bonding equipment can select electric iron, bonding machine, press machine, oven, special press machine, molds, ultrasonic heating and electromagnetic induction heating etc.

d. Pressing conditions include appropriate temperature, certain press and lasting time. Pressing condition selection shall be appropriate. Thus, the bonding strength is high and clothes quality is good. Generally, pressing temperature shall be higher than the melting point of adhesive.

Technical Indicators of Product:

1. Appearance: It has transparent film with certain strength and elasticity, and is lined with release paper. (Another type is mesh film, which is mainly used for hot melt recombination of textile fabrics. Products after recombination are soft and breathable)

2. Processing temperature: 80-140° C.
3. Processing pressure: 0.5-15 kg/c m².
4. Processing Time: 5-20 sec
5. Stretching resistance: 1 CM resistance is up to 6 KG Component and circuit can be bonded effectively when the temperature is at 100-110° C. Chemical fiber cloth bonding shall be heated to 120-130° C. The cloth may be charred if the temperature is too high and it shall pay attention to temperature control. Or ultrasonic wave and electromagnetic wave to melt hot melt film in low temperature. If pure cotton cloth is bonded, it can be heated to 120-150° C. Hot melt film thickness, covered oil separation paper, heating time, and pressure will affect the bonding effects.

Adding the heat melt adhesive film to cloth is to heat the circuit board and fix it on packaging cloth. Then stick, sew and paste on clothing cloth or heat it to fix on the clothing cloth. Additionally, the circuit board can also be heated and fixed on the clothing cloth first and then stuck, sewn, or pasted on the packaging cloth or heated to be fixed on the packaging cloth. At the moment, the heat melt adhesive film is penetrated into the packaging cloth or clothing cloth to produce electronic packaging structure for cloth.

Additionally, during the process to install heat melt adhesive film circuit board on cloth, a clamp can be used to apply force. Electronic component characteristics can be used to verify the connection between electronic component and transmission line, it shows that the package is not perfect. The package can also be tested by dripping water or color liquid on it. The characteristics of the electronic component can be measured to check the insulation of packaging, for example, if the capacitances before and after package are different, the package is not perfect.

The invention takes the heat melt adhesive film circuit board to manufacture cloth electronic product. The method is to put manufactured the heat melt adhesive film circuit board on the packaging cloth first, and then cover oil separation paper on the circuit board to make the melt adhesive not stick on heating equipment. Then heat on one side of oil separation paper to melt the adhesive and stick the transmission lines on the packaging cloth together with the electronic component. After the oil separation paper is removed, place it on the pre-set packaging position of clothing cloth to take secondary recombination can also be completed by sewing, sticking, or gluing, pasting and other methods. Completed circuit board is located between the clothing cloth and packaging cloth. As the circuit board is covered by packaging cloth above, the circuit board will not be exposed to have a beautiful appearance. At the same time, the heat melt adhesive film is penetrated into the packaging cloth and clothing cloth after melting. After the packaging is completed, overall structure formed by the heat melt adhesive film and cloth is extremely firm (as in FIG. 26A). In specific application, it can lead the conductor in the package body, and fix it in the clamp. Two ends are implemented pulling force to rub repeatedly. Take the conductor clamp as detection port, and read the electronic signal in the packaging body to take inspection. In inspection, it can drip water on the packaging body surface to check the insulation performance of packaging (as in FIG. 26B). After the inspection is completed, it can cut the tested conductor along the edge of packaging body or cut together with the edge of packaging body (as in FIG. 26C).

Figure 27:
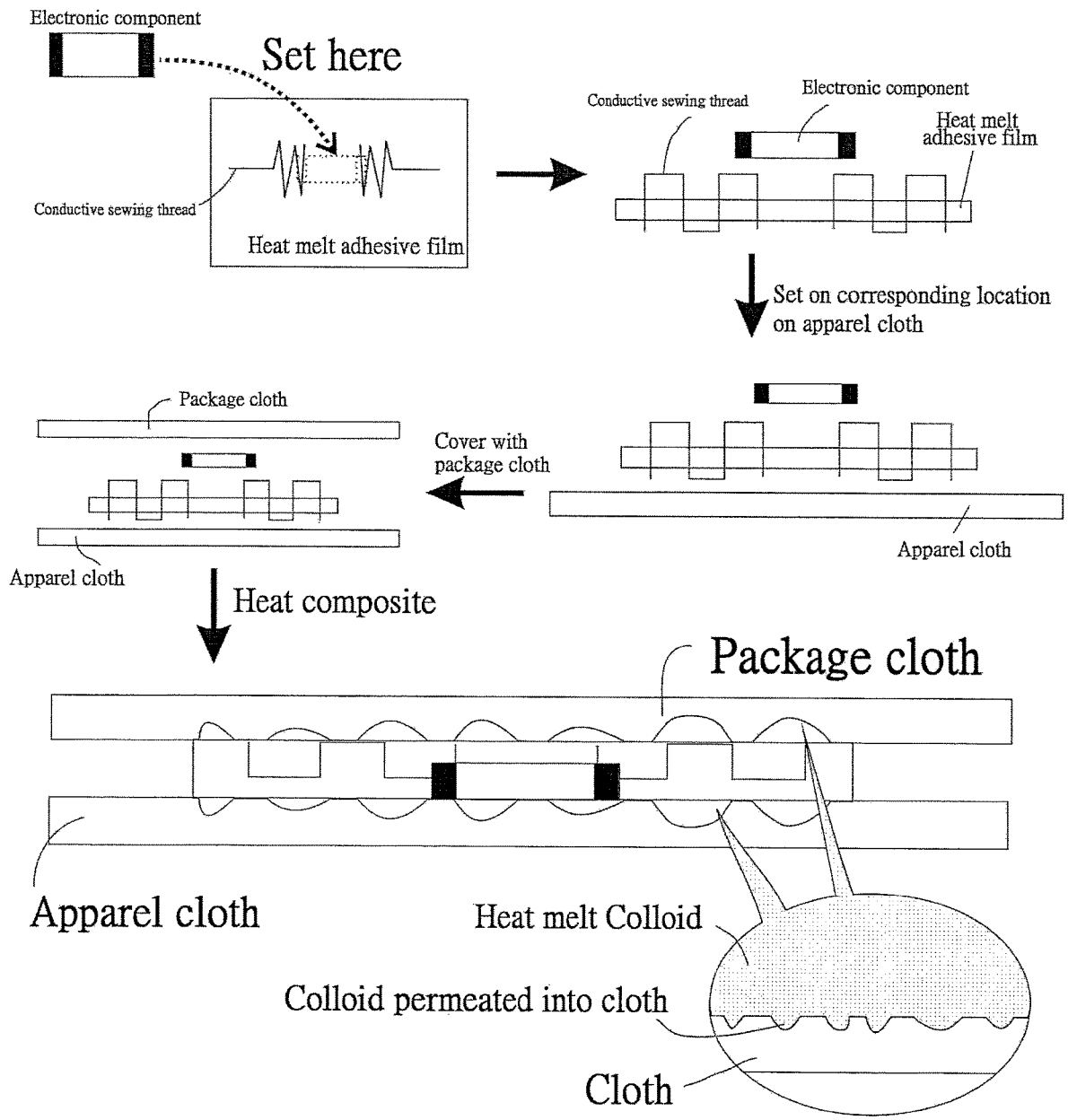
FIG. 27 illustrates the heat melt adhesive film circuits, electronic modules, the cloth, and the simultaneous composite packaging.

Another method of the invention which takes the adhesive circuit board to manufacture electronic product of cloth is to take simultaneous recombination and packaging of the heat melt adhesive film circuit, electronic component and cloth. The circuit board is the heat melt adhesive film with transmission line. Place the electronic component to enable the conductive region of electronic component contact with the conductive region of transmission line. Then place packaging cloth or clothing cloth above or below the circuit board to be heated and fixed, so that the electronic component is connected with the transmission line. At the same time, the heat melt adhesive film is permeated in packaging cloth or clothing cloth to produce packaging effect. Under the permission conditions of equipments (which requires computerized pattern machine and gang drilling machine), the method place the electronic component on the hot melt film with conductor and then place on corresponding position of clothing cloth. Then take heating recombination after packaging cloth is covered. All procedures are completed once (as in FIG. 27). In this way, it can reduce manufacturing cost and time greatly.

Furthermore, the method of invention to manufacture electronic product can also package individual component with conductive fabrics and then install it to other circuit. The circuit board includes one or minor electronic components. After it is heated and fixed with packaging cloth, an individual packaging component is produced. Then on clothing circuit, sew transmission line on individual packaging component to contact the clothing circuit with all individual components to produce a large scale circuit board.

As the method is to manufacture circuit board on clothes, in practical application, if it needs to manufacture equal side circuit board with human body or overall large size circuit, the above stated method is still available. If semi-finished product size is large in manufacturing and packaging process, it will increase manufacturing difficulty and costs undoubtedly. It is manufactured via separating all parts to make the conductor cloth bond on the hot melt film. Then place all individual components on the film and cover cloth above and below. Take heating and recombination to make electronic components connect with circuit board composed of conductive fabrics, and package it between the two layers of cloth. Then use conductive sewing thread to penetrate the structure and make the packaging circuits of all electronic components connect with other circuits (as in FIG. 28). The advantage of the method is to reduce the packaging volume of overall circuit. During batch production, event it is medium and small size thermal combination equipment, it can also produce large size circuit board. Furthermore, all plug-ins are modular production and installation. When one individual module has accidental damage, it will not make the entire circuit board scrap. It only needs to replace the damaged part. This can further improve the yield in batch production, thereby reducing the production costs.

In addition, invention can also use one cloth to complete the package. The packaging cloth is part of clothing cloth, i.e. the clothing cloth itself is packaging cloth.

Figure 29:
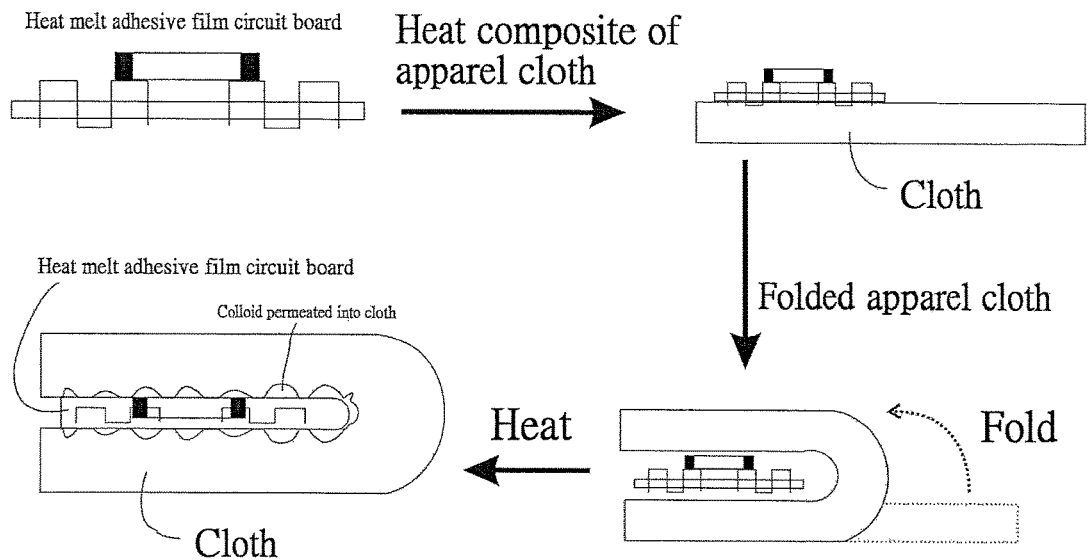
FIG. 29 illustrates the complete encapsulation of the cloth.

The method is to cooperate with traditional clothing production process, and it can also use clothing cloth as packaging cloth. Recombine adhesive circuit board initially at the clothing cloth pre-set position. Then fold the cloth reversely to enable the circuit board in the cloth. Then take secondary recombination, and it can also be completed by sewing, sticking or pasting methods, or it can place the adhesive circuit board on clothing cloth preset position after reverse folding. Then use only once heating and recombination to install the circuit board (as in FIG. 29).

The invention can achieve multilayer structure application. The circuit boards made of adhesive film have connection points and boards can be stacked such that the connection points can be overlapped to produce a multilayer circuit board structure textile. At the same time, insulation materials can also be placed between the upper layer and lower layer.

Every layer of the circuit board made of heat melt adhesive film has at least one connection points and can be overlapped. It uses transmission line to connect the connection points of upper and lower layers to produce multilayer circuit board structure of textile. At the same time, insulation materials can also be placed between the upper layer and lower layer.

Figure 30A:
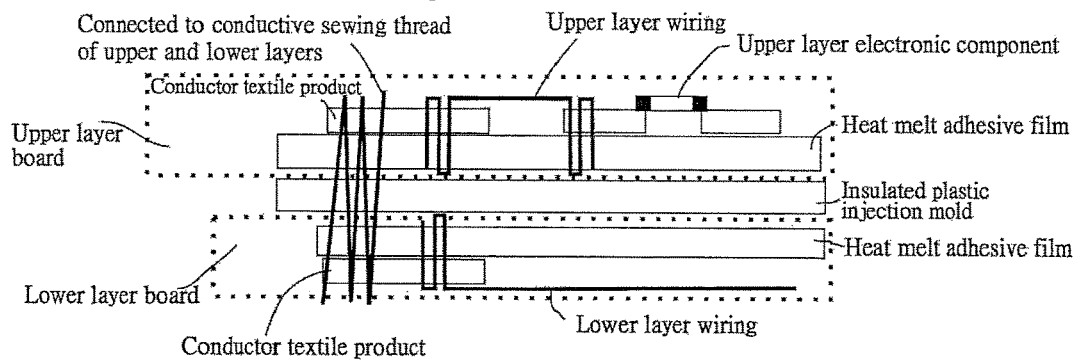
FIG. 30A and FIG. 30B illustrate the application of a multi-level structure.
Figure 30B:
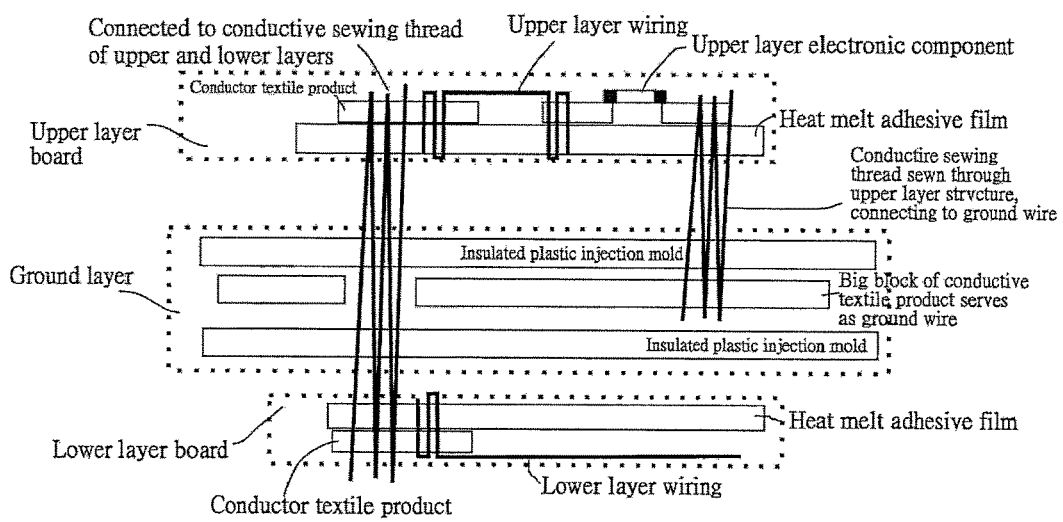

The method can be used with conventional multilayer design of the electronics industry in practical application. An insulating plastic film can be placed between the upper and lower plates (which can also be replaced by fabrics, oil separation paper, heat melt adhesive film, glass fiber cloth). Previously introduced packaging technology is used to package circuit board. Then use transmission line to penetrate connection points of upper and lower plates and connect the upper and lower layers of circuits. Multilayer structure diagram is formed (as in FIG. 30A). Or grounding layer is added between the upper and lower plates and transmission line is used to penetrate the layer to provide connection points for upper and lower plates, so as to achieve commonly-used single point grounding structure of traditional electronic circuit design (as in FIG. 30B). It enables the electronic engineer play freely as much as possible in the actual circuit design.

Figure 31A:
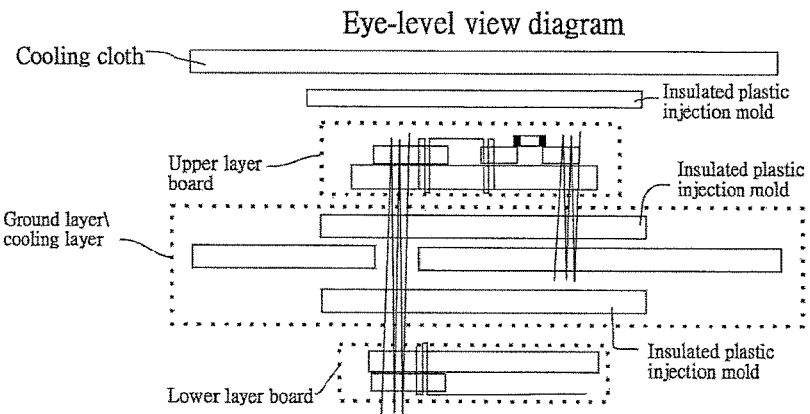
FIG. 31A and FIG. 31B illustrate the multi-level structure loaded with heat rejection constructs.
Figure 31B:
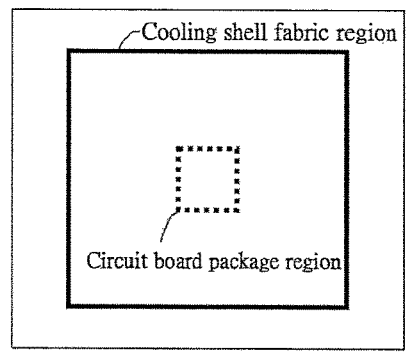

The invention can manufacture multilayer plate with heat radiation structure. When multilayer plate is produced, as some power consumption of circuit structure is greater, sometimes, it may generate more heat in circuit. In order to prevent affecting normal operation of product, heat radiation structure can be added in the circuit structure with larger power consumption. Take the grounding circuit board structure in FIG. 30B as an example. As the conductive textile has good thermal conductivity, it can increase the conductive textile area of the grounding layer and make it far beyond the packaging region of circuit board, so that the grounding layer also has the function heat radiation layer. At the same time, on the upper layer of packaging body, it can also cover heat radiation cloth to enable it has insulation. (If conductive fabrics are used as covered heat radiation cloth, it requires adding a layer of insulation plastic film above the upper plate.) (It can also be replaced by fabrics, oil separation paper, heat melt adhesive film, glass fiber cloth). (As in FIG. 31A to 31B)

For part multilayer board manufactured by the invention, if the heat melt adhesive film produced circuit board requires electromagnetic shielding interference, a kind of conductive material can be set below, and it has an insulating material layer between the conductive material and circuit board. At the same time, it has a conductor sewing through the three layers to generate electromagnetic protection.

Figure 32A:
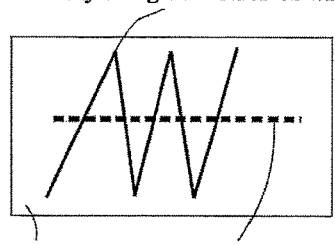
FIG. 32A and FIG. 32B illustrate a corner of a multi-level structure.
Figure 32B:
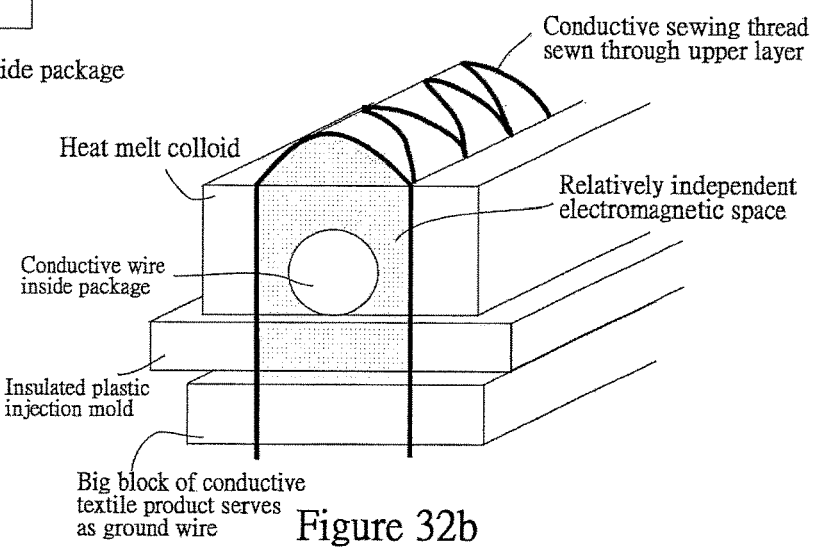
Figure 33:
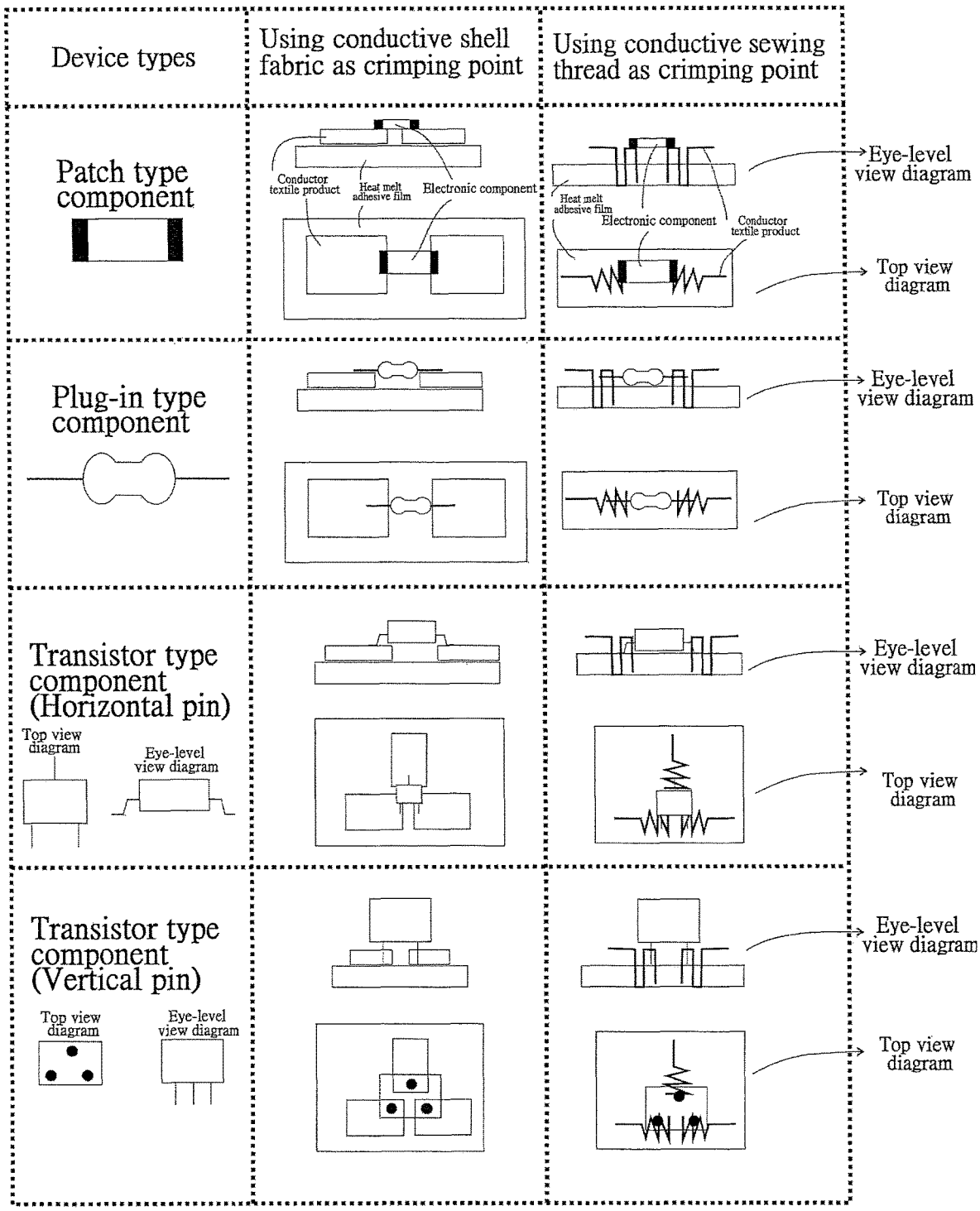
FIG. 33 illustrates the method of applying various types of electronic modules to real life.

Due to process limitation in traditional electronics industries, if it requires one or several conductors in the circuit board providing electromagnetic protection, it shall manufacture a piece of recombination layer with the same size of circuit board and add the layer on the board regardless of the actual area. As the invented cloth circuit board is manufactured by sewing soft conductive materials via sewing machine, it can use computerized embroidery machine to penetrate the upper layer conductive sewing thread at the packaging conductor position which requires electromagnetic shielding and sew intensively along the two sides of route to achieve electromagnetic protection structure of part multilayer board. (This principle is similar to multi-point grounding of conventional electronic circuit design. When this process is used in textile circuit board, the number of grounding point shall be far more than conventional electronic circuit boards). See FIGS. 32A and 32B.

The invention has different practical using methods for different types of electronic components. Currently, the use electronic component shapes have 4 classes: surface-mount class components, plug-in class components, horizontal pin transistor class components), vertical pin transistor class components. In specific application, conductive fabric can be taken as compressing point, and conductive point sewing thread can also be taken as compressing point to take packaging according to the packaging method introduced from FIG. 25A to FIG. 25C.

Reinforcing method of compressing point in the invention can be connected with conductive region of electronic component via the heat melt adhesive film produced transmission line, and can add conductive adhesive or low temperature soldering tin. If low temperature soldering tin is used, first, heat the low temperature soldering tin and melt it on the conductive region of electronic component. Then heat and fix the electronic component with low temperature soldering tin and adhesive component, such as conductive fabric. The permeation of low temperature soldering tin is enlarged to strengthen the connection of transmission line and electronic component. Above low temperature soldering tin can also be melted with the connection of transmission line for the heat melt adhesive film, and heated and fixed with the electronic component, which has the same effect. If conductive adhesive is added, it can be added when the packaging cloth or clothing cloth is heated and fixed, so as to make the connection of transmission line and connective region of electronic component more effective.

Figure 34:
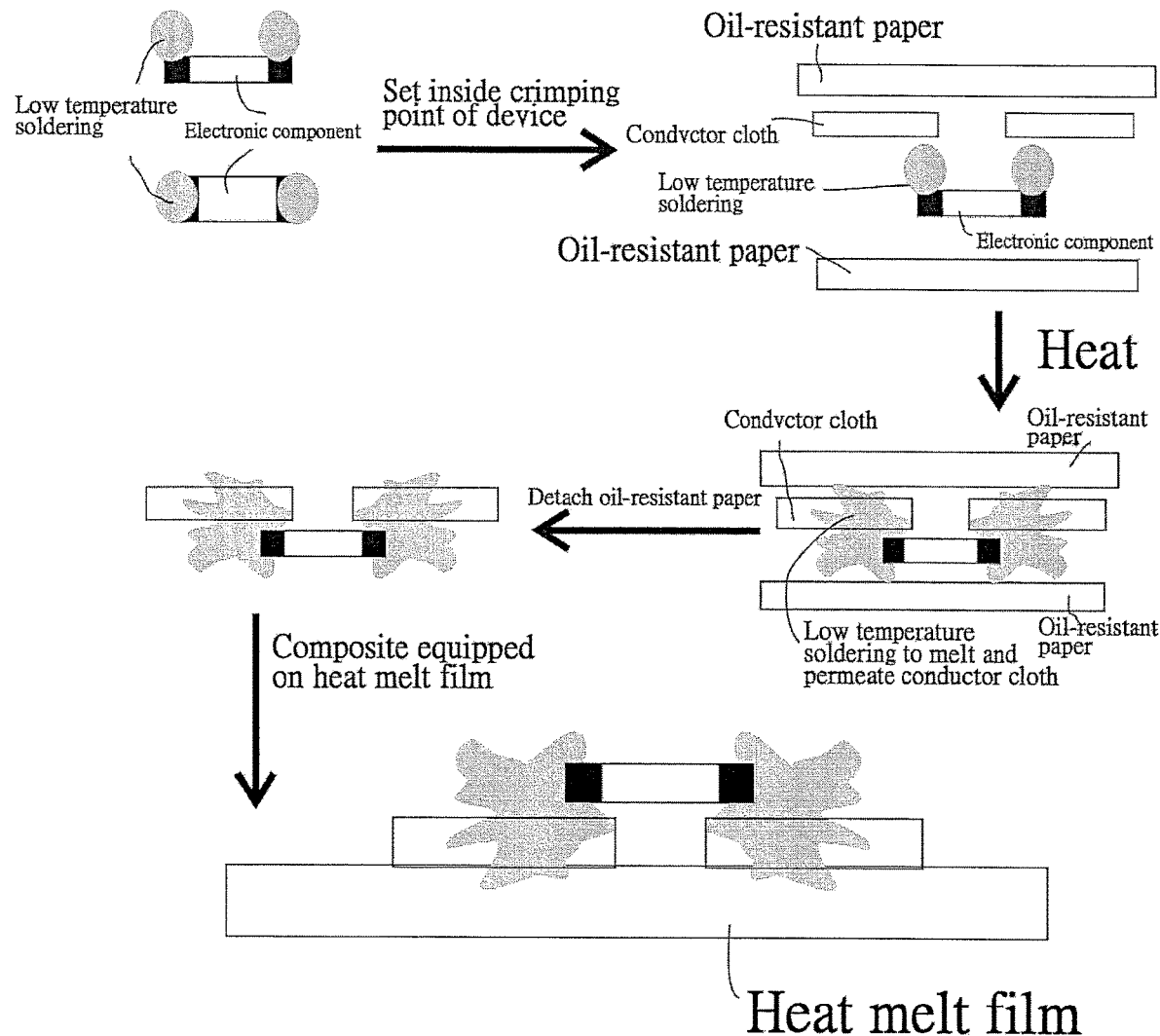
FIG. 34 illustrates the method of strengthening the joints.

This method has higher requirement in the working condition of electronic component. It can add conductive adhesive or low temperature soldering tin in the conductive region of electronic component or at the transmission line pin when the pad of electronic component and circuit connection are extremely stable to stick or weld the conductive region of electronic component or pins firmly in the fabric circuit. First, add low temperature soldering tin in the conductive region of electronic component (or at the transmission line pin), and cover oil separation paper above and below. Heat the soldering tin and make the soldering tin melt permeate into the conductive cloth to weld the conductive region of electronic component firmly with the conductive cloth. Then recombine with the heat melt adhesive film (as in FIG. 34). If conductive adhesive is added, the conductive adhesive can be added when it is heated and recombined with the packaging cloth. If low temperature soldering tin is used, it must weld conductive fabric appropriately before entering into recombination procedures. As the melting point of low temperature soldering tin is 138° C., it must control the temperature within 140-150° C. and heating time as 5 seconds during the welding procedure. If the heating time is too long or temperature is too high, it will burn up the conductive cloth. If the temperature is lower than 138° C. or the heating time is insufficient, the low temperature soldering tin will not be melted completely, and it may cause infirm welding. In all following heating procedure, it must control the temperature within 120-130° C. accurately. It cannot melt soldering tin simultaneously when the heat melt adhesive film is melted. Once the soldering tin is melted in heating and recombination, cohesion and surface tension in liquid status are far less than the adhesive at the same temperature. The soldering tin will be squeezed out of conductive cloth permeated in previous step of welding to cause defective component contacting.

For the application method example of the invention, packaging cloth and clothing cloth of peripheral packaging structure can use sewing, sticking and pasting and use ultrasonic or electromagnetic waves further to increase packaging and anti-interference effect.

Figure 28:
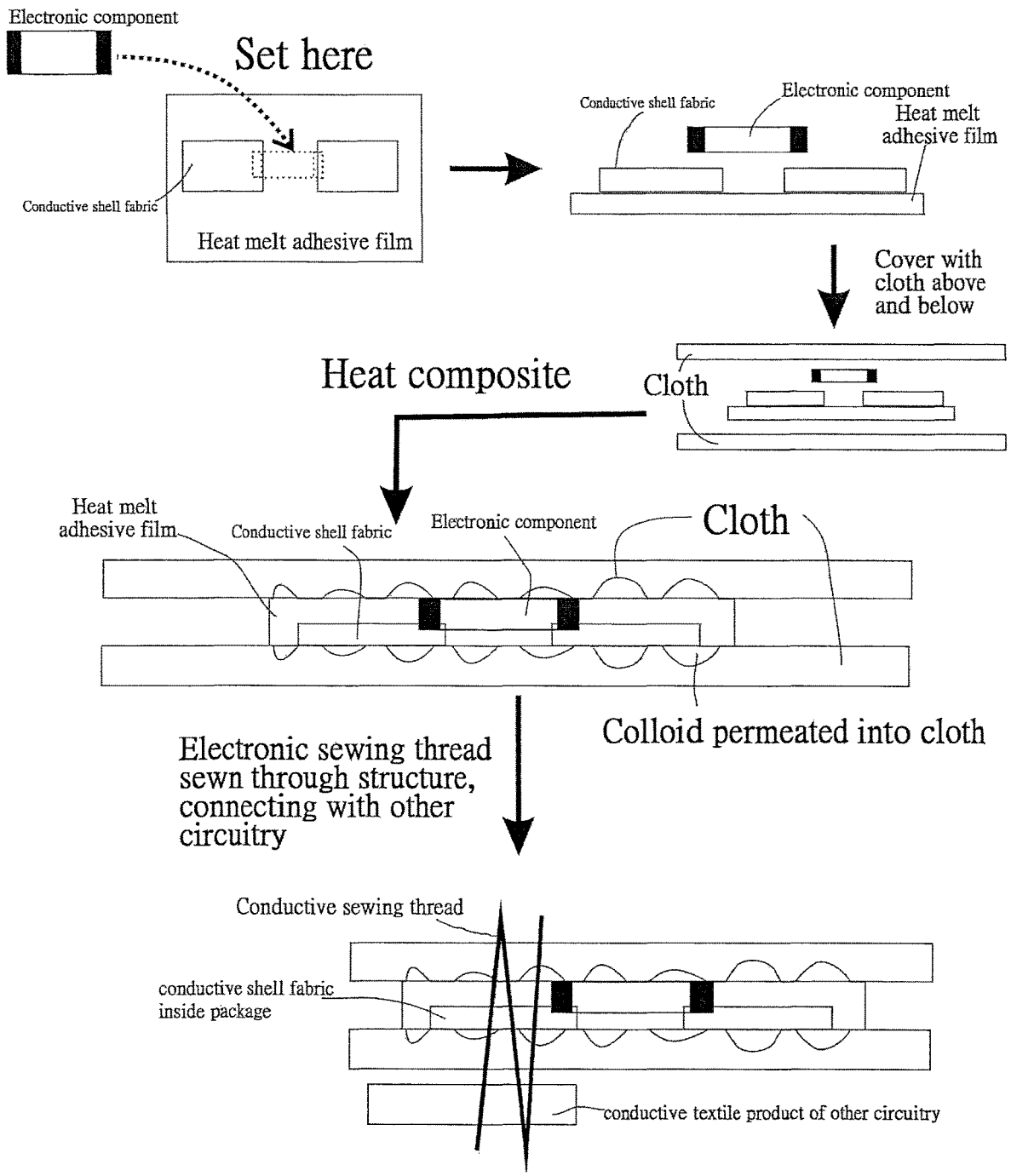
FIG. 28 illustrates how monolithic component and conductive textiles are packaged and then are loaded to other routes.

It is the specific application of FIG. 28 stated method. An element package containing 2 resistors is manufactured by using the packaging structure of FIG. 28, and common sewing is used at the peripheral of package for reinforcement to protect and prevent internal of circuit package from suffering tensile force when it is pulled by tensile force. (It can also use ultrasonic wave bonding or electromagnetic waves bonding to achieve equivalent protection mechanism.) Then it uses transmission line to penetrate the package and connect with the circuit on clothing, enabling to achieve conventional machine washing textile circuit products.

Figure 35A:
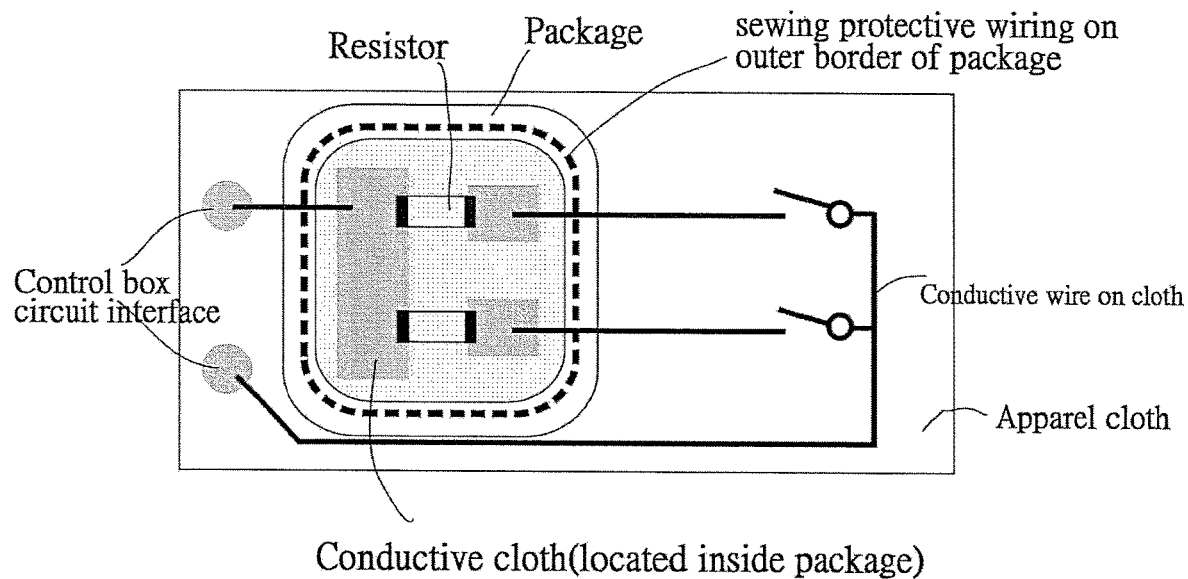
FIG. 35A and FIG. 35C illustrate examples of application methods.
Figure 35B:
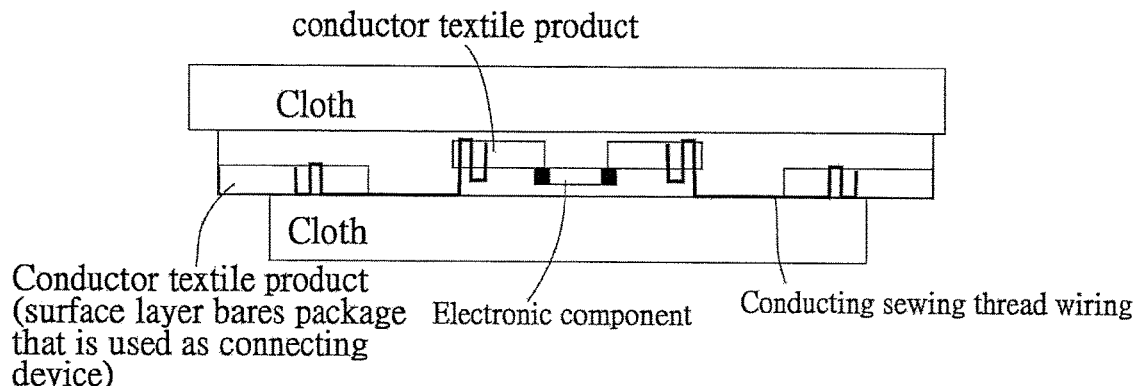
Figure 35C:
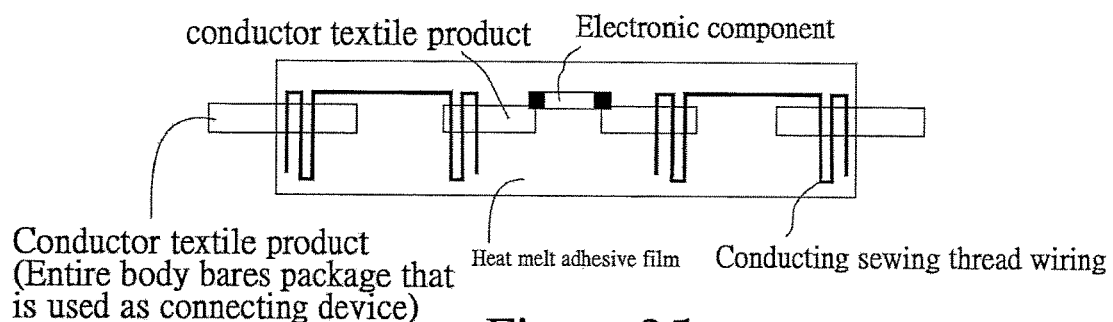

Or in packaging, conductor interface is set aside to make the interface expose the package. Then sewing method can be used to install on other circuits or connect with control box for using (as in FIG. 35B and FIG. 35C). FIG. 35*b* is conductive fabric surface exposed package and it is taken as connector. The connector can also be conductive silicone, conductive rubber, conducting strip, fastener components (such as: mother button or snap button), conductive adhesive Velcro (Velcro), conductive fabric (such as silver fiber fabrics), bus bar (such as stainless steel bars) or conducting multi-molecular material. All are suitable for control box interface part as in FIG. 35A. FIG. 35B is conductive fabric overall exposed package and it is taken as connector. It is suitable to use sewing conductive thread to install overall exposed conductive fabrics to other circuits. Considering if the package surface cloth is wet, it may connect two connectors. Therefore, in practical application of the structure, min horizontal distance between the two connectors shall be no less than 3 cm.

Batch production used equipment of all processes for the invention is computerized embroidery machine, as in FIG. 36A. It can use transmission line, such as conductive sewing line, to sew pre-designed circuit routing plan on the heat melt adhesive film or cloth, and it can be sewn by multiple machines. Currently, the equipment has been widely used in cloth production, and the technology is quite mature. FIG. 36B is gang drilling machine. The equipment is applied to arrange large quantity of hot drilling particles originally to constitute a decorative pattern. The invention can use the equipment to place electronic components (such as paster components) on hot melt circuit board automatically according to the preset programs. Furthermore, multiple machines can be worked simultaneously. FIG. 36C and FIG. 36D are drum-type thermal combination machines. The equipments use heating roller and feeding roller to heat and convey hot melt film circuit board or oil separation paper and fabrics etc, so as to achieve heating packaging.

Despite the preferred implementation examples of the present invention have been illustrated and described, technicians in the field understand various changes and modifications can be made without departing from the true scope of the invention, and equivalents can be used to replace the components. For example, for description purposes, although surface mount devices (SMD) and through hole installed electronic components shapes with pin have been shown, it can be understood that the present invention is able to support other shapes of electronic components of the conductive region. Thus, conductive region shape of electronic component in the attached figure should not limit the scope of invention.

The above description is just a better implementation example of the invention. It does not limit on any forms to the invention. Although the invention has been disclosed by a better implementation example, it is not used to limit the invention. Any technicians who are familiar with the profession can use the above disclosed technical contents to make little changes or modifications as equivalent implementation example with equal changes without departing from the scope of the present application. However, any simple modification, equivalent changes and alteration to above implementation example based on the technical substances of the invention without departing from the present invention still belong to the technical solution scope of present invention.

The invention claimed is:
1. A method for fabricating electronic cloth comprising:
providing a first cloth layer, at least one hot melt adhesive film and a second cloth layer;
forming circuit wiring on the at least one hot melt adhesive film to provide a film-based circuit board with the at least one hot melt adhesive film as a substrate;
providing at least one electronic component comprising a conductive region and connecting the conductive region to at least one transmission line on the at least one hot melt adhesive film, where a first face of the at least one electronic component is attached to the at least one hot melt adhesive film, wherein a second face of the at least one electronic component, which is opposite to the first face, is attached to the second cloth layer such that the at least one electronic component is fixed between the first cloth layer and the second cloth layer and unmovable with respect to the first cloth layer and the second cloth layer; and
heating the at least one hot melt adhesive film so that the at least one hot melt adhesive film is attached to the first cloth layer and the second cloth layer to package, isolate and secure the at least one electronic component, wherein the at least one hot melt adhesive film is sandwiched by the first cloth layer and the second cloth layer and there is no gap formed therein;
wherein the first cloth layer and the second cloth layer are bonded to the conductive region of the at least one electronic component by the at least one hot melt adhesive film; and
wherein a connection between the conductive region of the at least one electronic component and the at least one transmission line is completely isolated by and completely in contact with the at least one hot melt adhesive film.

2. The method for fabricating electronic cloth as described in claim 1, wherein the at least one hot melt adhesive film forms a plurality of circuit boards that are stacked one above another to produce a multilayer textile structure of circuit boards and have the at least one transmission line to connect the circuit boards, wherein an insulation material is placed between the circuit boards having the at least one transmission line to connect the circuit boards or a grounding layer is disposed between an upper layer board and a lower layer board, so as to achieve grounding structure.

3. The method for fabricating electronic cloth as described in claim 2, wherein an insulating plastic film, fabrics, oil separation paper, a hot melt adhesive film, or a glass fiber cloth is disposed between the upper layer board and the lower layer board.

4. The method for fabricating electronic cloth as described in claim 1, further comprising checking packaging insulation of the at least one electronic component by dripping water or colored liquid on the at least one electronic component, or by measuring at least one characteristic of the at least one electronic component.

5. The method for fabricating electronic cloth as described in claim 1, wherein the method used to couple the conductive region of the at least one electronic component and the at least one transmission line is also used for connecting between transmission lines or between electronic components.

6. The method for fabricating electronic cloth as described in claim 1, wherein a conductive material is provided below the at least one electronic component, and an insulating material layer is provided between the conductive material and the at least one electronic component to generate electromagnetic shielding.

7. The method for fabricating electronic cloth as described in claim 1, wherein an electronic equipment is used to measure whether the at least one electronic component is in good contact with the at least one transmission line and whether a contact between the at least one electronic component and the at least one transmission line changes under an effect of external force to adjust a relation between the at least one electronic component and the at least one transmission line or between the at least one electronic component and another electronic component or between two transmission lines.

8. The method for fabricating electronic cloth as described in claim 1, wherein the at least one electronic component functions as a pressure sensor or a tension sensor, wherein an output value has different results due to a closing degree of the conductive region and the at least one transmission line, or a closing degree of the conductive region and another conduction region, or a closing degree of the at least one transmission line and another transmission line, wherein the closing degree produces variation as an external pressure or tension changes.

9. The method for fabricating electronic cloth as described in claim 8, wherein non-conductive yarns or materials are added between the conductive region of the at least one electronic component and the at least one transmission line to increase a sensing value of the pressure sensor or the tension sensor.

10. The method for fabricating electronic cloth as described in claim 1, wherein the at least one transmission line comprises at least one selected from a group consisting of twin-lead wire, parallel multi-conductor, coaxial wire, ribbon line, single-core wire, multi-core and multiple strands, conductive fabric, conductive strips, stainless steel wire, conductive wire, silver fiber, conductive polymer material, encapsulated conductive line, and enameled wire; wherein the at least one transmission line is made of metal fibers comprising copper, gold, silver, nickel, aluminum, iron, stainless steel, or nickel alloy, or made of non-conductive fibers embedded or coated with conductive materials comprising conductive carbon, nickel, copper, gold, silver, titanium, or conductive wires; or wherein the at least one transmission line has an insulator outside of a conductor.

11. The method for fabricating electronic cloth as described in claim 1, wherein the at least one electronic component is selected from a group consisting of a resistance, a capacitance, an inductance, a switch, a diode, amplifiers, a battery, sensors for temperature/breathing/heartbeat, an electromyogram, an acceleration gauge, a gyroscope, a camera, temperature sensors, chemical sensors, biological sensors, pressure sensors, sound sensors, electric fields sensors, magnetic fields sensors, acceleration and/or environmental conditions sensors, power sensors, heat sensors, electromagnetic radiation and/or sound sensors, an infrared and/or wireless transmitter and/or receiver, an imager, a CCD imager, a thermocouple sensor, a cooler, a heater and/or generators, LCD components, an electro-luminescent element, an organic light emitting element, an OLED, electrophoretic elements, an LED, piezo-electric element and/or sensors, a microphone, speakers, processors, digital signal processors, microprocessors, microcontrollers, a CPU, analog-to-digital converters, digital-to-analog converters, a data production equipment, a data application equipment, a process equipment, a switchboard, a man-machine interface device, an input device for an individual, signal lights and/or flashing lights, solar cells, a photovoltaic power generation equipment, an electrode and addressing devices.

12. The method for fabricating electronic cloth as described in claim 1, wherein the at least one hot melt adhesive film comprises one or more selected from a group consisting of polyamide hot melt adhesive film (PA), polyester hot melt adhesive film (PET), polyurethane hot melt adhesive film (PU), thermoplastic polyurethane (TPU), polyolefin hot melt adhesive film (PO), and ethylene-vinyl acetate copolymer hot melt adhesive film (EVA).

13. The method for fabricating electronic cloth as described in claim 1, further comprising using one or more selected from a group consisting of sewing, sticking and pasting, and using ultrasonic or electromagnetic waves to package the at least one electronic component.

14. The method for fabricating electronic cloth as described in claim 1, wherein low temperature soldering tin, conducting cloth, or conducting glue is added to connect the at least one transmission line with the conductive region of the at least one electronic component.

15. The method for fabricating electronic cloth as described in claim 1, wherein a peripheral of an individual packaging component is processed by sewing, sticking, pasting, ultrasonic waves, or electromagnetic waves to reinforce packaging and improve anti-interference effect.

16. The method for fabricating electronic cloth as described in claim 1, wherein the at least one electronic component is disposed on the circuit board formed by the at least one hot melt adhesive film in such a way that the conductive region of the at least one electronic component is in contact with the at least one transmission line;
   wherein the first and second cloth layers then are disposed above and underneath the circuit board and are heated to be fixed with the circuit board, so that the at least one electronic component is connected with the at least one transmission line; and
   wherein the at least one hot melt adhesive film is attached to the first or second cloth layer to achieve a packaging effect.

17. The method for fabricating electronic cloth as described in claim 1,
   wherein the first cloth layer or the second cloth layer has a material to connect the conductive region of the at least one electronic component and the at least one transmission line; and
   wherein the material is conductive silicone rubber, a conductive fabric, a conductive rubber, a conductive cloth, a conductive bar, a conductive polymer material, or conductive adhesive tape.

18. The method for fabricating electronic cloth as described in claim 1, wherein the circuit board comprises the at least one electronic component, and forms an individual packaging component after being heated and fixed to the first cloth layer; wherein the individual packaging component is set onto the second cloth layer to connect with another individual packaging component by the at least one transmission line, creating a large scale circuit board.

19. The method for fabricating electronic cloth as described in claim 1,
wherein the circuit board is secured to the first cloth layer or the second cloth layer using heat pressing; or
wherein the circuit board is secured to the first cloth layer or the second cloth layer by:
attaching and covering the at least one hot melt adhesive film on one of the first cloth layer and the second cloth layer;
heating the at least one hot melt adhesive film to a melting temperature;
attaching and covering the other one of the first cloth layer and the second cloth layer on the at least one hot melt adhesive film with pressure; and
cooling the at least one hot melt adhesive film, the first cloth layer, and the second cloth layer so that the at least one hot melt adhesive film solidifies; and
wherein an electric iron, a bonding machine, a press machine, an oven, a mold, ultrasonic heating, or electromagnetic induction heating is used to secure the circuit board to the first cloth layer or the second cloth layer.

20. The method for fabricating electronic cloth as described in claim 1, wherein a conductive magnetic material is used to prevent electromagnetic interference.

21. The method for fabricating electronic cloth as described in claim 1, wherein the at least one electronic component or the at least one transmission line is fixed to the hot melt adhesive film via glue or adhesive paste.

22. The method for fabricating electronic cloth as described in claim 1, wherein the first or the second cloth layer is made of cotton, nylon, plastic, or linen.

23. The method for fabricating electronic cloth as described in claim 1, wherein a conductive wire is provided on an upper layer of a signal wire, providing a shield layer that prevents electromagnetic interference (EMI).

24. The method for fabricating electronic cloth as described in claim 1, wherein conductive wires are sewn alongside the at least one transmission line or the at least one electronic component in positions that need electromagnetic interference shielding.

25. A method for fabricating electronic cloth comprising:
providing a first cloth layer, a second cloth layer and at least one electronic component comprising a conductive region coupled to a transmission line on a hot melt adhesive film to form a circuit board, at least part of the transmission line being buried in the hot melt adhesive film;
wherein:
a first face of the at least one electronic component is attached to the hot melt adhesive film;
a second face of the at least one electronic component, which is opposite to the first face, is attached to the second cloth layer such that the at least one electronic component is fixed between the first cloth layer and the second cloth layer and unmovable with respect to the first cloth layer and the second cloth layer;
the transmission line and the at least one electronic component are directly sewn, by a computerized sewing machine according to a pre-arranged routing plan, on the hot melt adhesive film;
a thermal combination machine is used to package the circuit board by heating and feeding the circuit board formed by the hot melt adhesive film and by sandwiching the circuit board with an oil separation paper or fabrics, and there is no gap formed in the hot melt adhesive film.

26. The method for fabricating electronic cloth as described in claim 25, wherein a circuit routing layout is thermal printed or ink ejected on the hot melt adhesive film prior to sewing, sticking, or pasting the transmission line and the at least one electronic component on the hot melt adhesive film according to the circuit routing layout.

27. The method for fabricating electronic cloth as described in claim 25, wherein the hot melt adhesive film comprises one or more selected from a group consisting of polyamide hot melt adhesive film (PA), polyester hot melt adhesive film (PET), polyurethane hot melt adhesive film (PU), thermoplastic polyurethane (TPU), polyolefin hot melt adhesive film (PO), and ethylene-vinyl acetate copolymer hot melt adhesive film (EVA).

28. The method for fabricating electronic cloth as described in claim 25, wherein the circuit board functions as a pressure sensor or a tension sensor.

29. The method for fabricating electronic cloth as described in claim 25,
wherein the transmission line passes through or comes into contact with a conductive silicone rubber, a conductive strip, a conductive rubber, a conductive cloth, or a conductive bar, and is sewn on the hot melt adhesive film; and
wherein the conductive region of the at least one electronic component is embedded in or in contact with the conductive silicone rubber, the conductive strip, the conductive rubber, the conductive cloth, or the conductive bar.

30. The method for fabricating electronic cloth as described in claim 25, wherein the thermal combination machine is a drum-type thermal combination machine using heating rollers and feeding rollers.

* * * * *